(12) United States Patent
Naya et al.

(10) Patent No.: US 7,643,156 B2
(45) Date of Patent: Jan. 5, 2010

(54) SENSOR, MULTICHANNEL SENSOR, SENSING APPARATUS, AND SENSING METHOD

(75) Inventors: Masayuki Naya, Ashigarakami-gun (JP); Takeharu Tani, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 316 days.

(21) Appl. No.: 11/663,739

(22) PCT Filed: Jun. 14, 2006

(86) PCT No.: PCT/JP2006/312371

§ 371 (c)(1),
(2), (4) Date: Mar. 26, 2007

(87) PCT Pub. No.: WO2006/135097

PCT Pub. Date: Dec. 21, 2006

(65) Prior Publication Data

US 2007/0263221 A1 Nov. 15, 2007

(30) Foreign Application Priority Data

| Jun. 14, 2005 | (JP) | ............................. 2005-173752 |
| Jun. 14, 2005 | (JP) | ............................. 2005-173976 |
| May 30, 2006 | (JP) | ............................. 2006-149712 |
| May 30, 2006 | (JP) | ............................. 2006-149713 |

(51) Int. Cl.
*G01B 9/02* (2006.01)
*G01J 3/45* (2006.01)
*G01N 21/41* (2006.01)
*G01N 21/43* (2006.01)
*G01N 21/00* (2006.01)

(52) U.S. Cl. ........................ 356/519; 356/454; 356/517; 356/436; 422/82.09

(58) Field of Classification Search ................. 356/436, 356/454, 480, 517, 519; 422/82.09
See application file for complete search history.

(56) References Cited

U.S. PATENT DOCUMENTS 5,218,426 A * 6/1993 Hall et al. .................... 356/517

(Continued)

FOREIGN PATENT DOCUMENTS

JP 6-167443 A 6/1994

(Continued)

OTHER PUBLICATIONS

Takayuki Okamoto et al., "Local plasmon sensor with gold colloid monolayers deposited upon glass substrates", Optic Letters, Mar. 15, 2000, pp. 372-374, vol. 25, No. 6.

*Primary Examiner*—Michael A Lyons
(74) *Attorney, Agent, or Firm*—Sughrue Mion, PLLC

(57) ABSTRACT

A new and novel sensor having a simple structure with high detection sensitivity. The sensor (S1) includes the following from measuring light (L1) input side in the order listed below: a first reflector (10) having semi-transmissive and semi-reflective properties; a translucent body (20); and a second reflector (30) having perfect reflection properties, or semi-transmissive and semi-reflective properties. The first reflector (10) and/or second reflector is brought into contact with a specimen, and the average complex refractive index varies with the specimen. Absorption properties for absorbing light having a particular wavelength are produced by these components, the properties of the measuring light (L1) are changed by the optical properties including the absorption properties, the output light (L2) is outputted from the first reflector (10) and/or second reflector (30), and the physical properties of the output light (L2) that vary according to the optical properties are detected.

29 Claims, 10 Drawing Sheets

U.S. PATENT DOCUMENTS

| | | | |
|---|---|---|---|
| 5,422,714 A * | 6/1995 | Fladd | 356/128 |
| 6,839,140 B1 * | 1/2005 | O'Keefe et al. | 356/436 |
| 7,097,250 B2 | 8/2006 | Rausch et al. | |
| 7,403,292 B2 * | 7/2008 | Tomaru | 356/517 |
| 2003/0132392 A1 | 7/2003 | Kuroda et al. | |
| 2008/0018890 A1 * | 1/2008 | Maity et al. | 356/301 |

FOREIGN PATENT DOCUMENTS

| | | |
|---|---|---|
| JP | 8-15133 A | 1/1996 |
| JP | 2000-356587 A | 12/2000 |
| JP | 2001-242072 A | 9/2001 |
| JP | 2003-268592 A | 9/2003 |
| JP | 2003-270132 A | 9/2003 |
| JP | 2004-232027 A | 8/2004 |
| JP | 2005-69893 A | 3/2005 |
| WO | WO 2005-095927 A1 | 10/2005 |

* cited by examiner

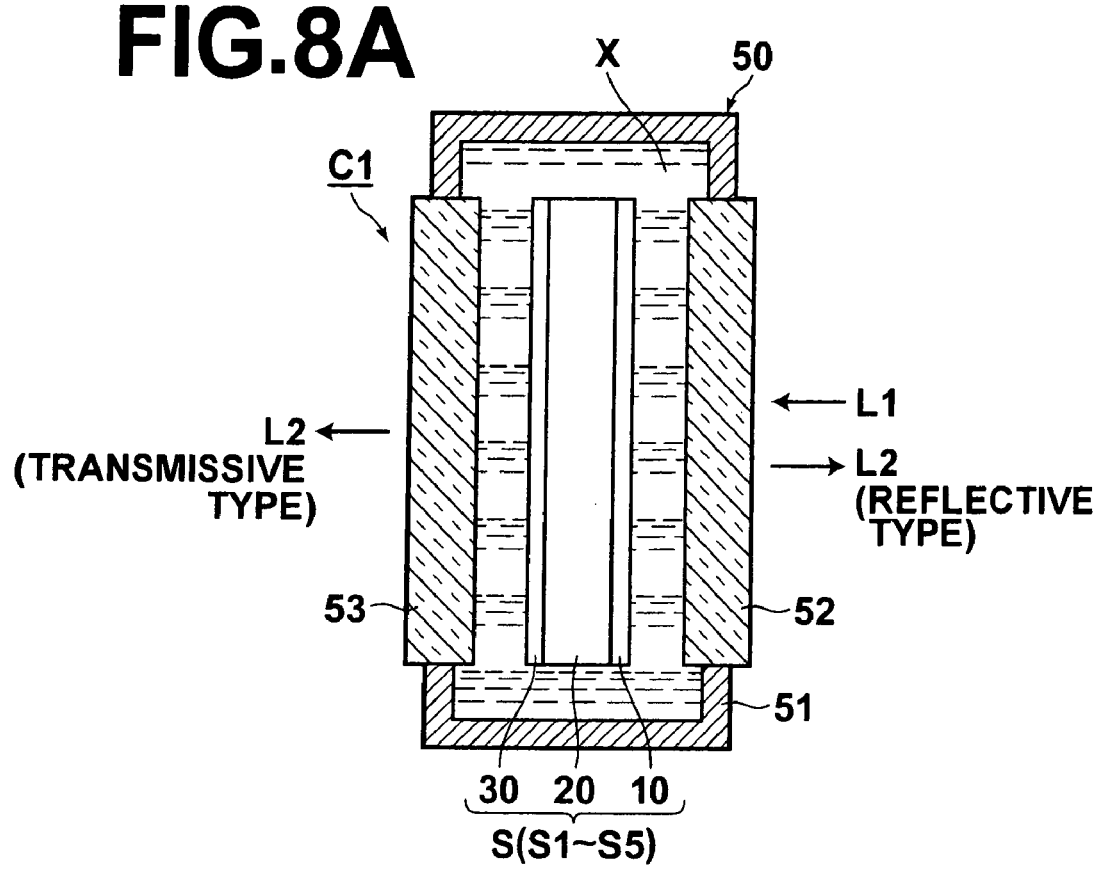
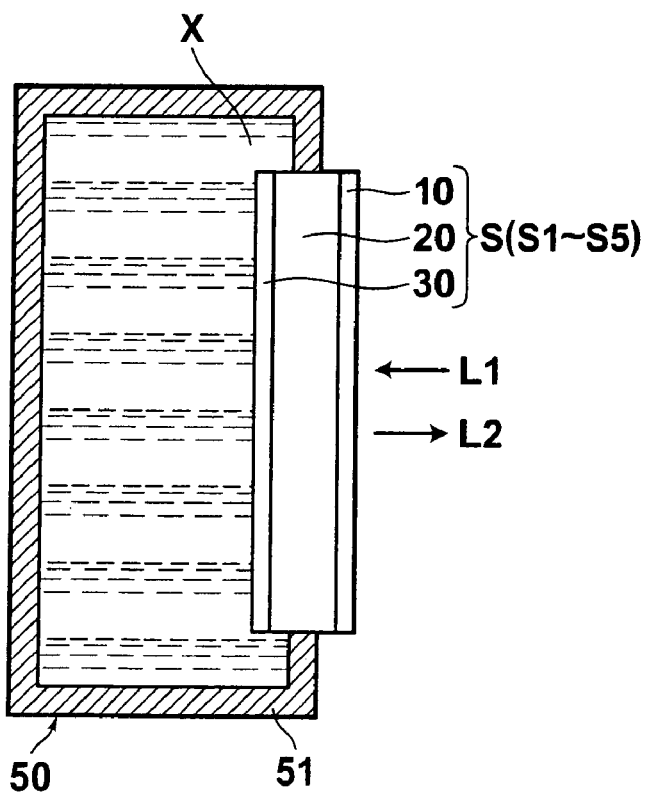

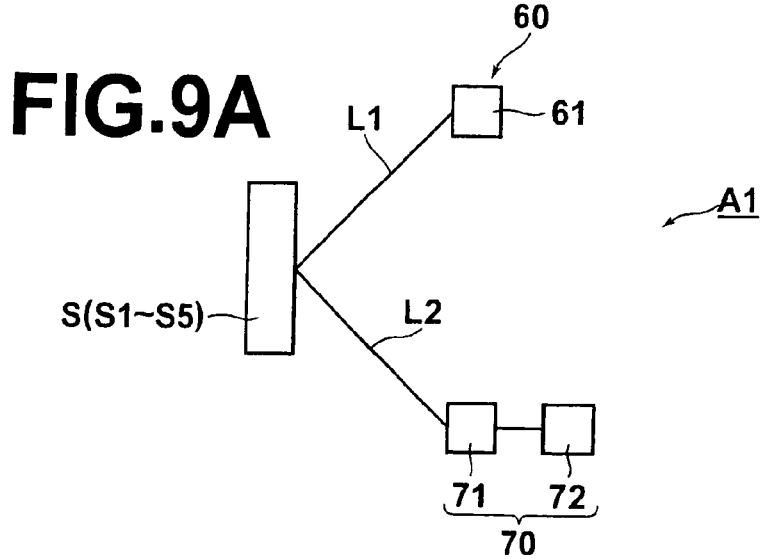
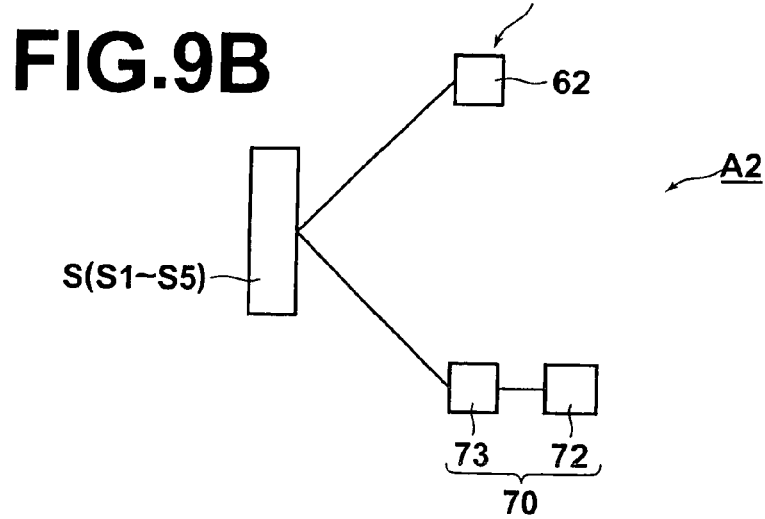
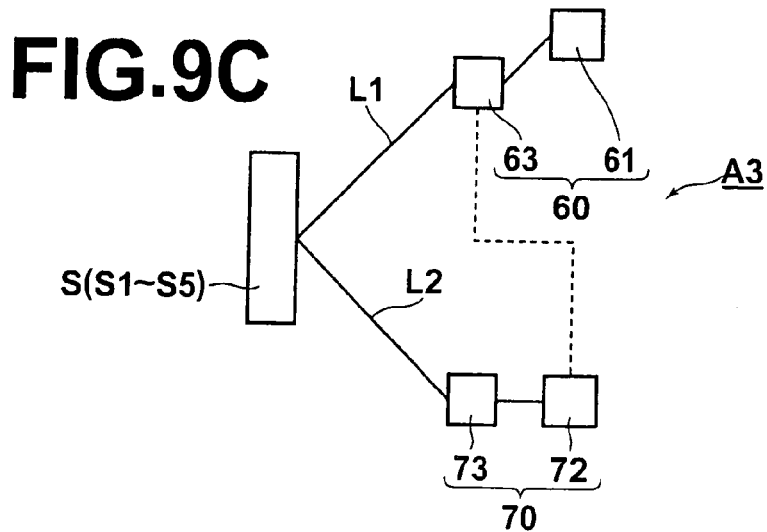

SENSOR, MULTICHANNEL SENSOR, SENSING APPARATUS, AND SENSING METHOD

TECHNICAL FIELD

The present invention relates to a sensor in which measuring light is inputted and outputted therefrom as output light after the physical properties thereof are changed by a specimen, and detected. It also relates to a multichannel sensor, a sensing apparatus, and a sensing method using the same.

BACKGROUND ART

As one of the sensors used for biomolecular analysis or the like, a sensor that makes use of the phenomenon in which the light intensity of the reflected light having a particular wavelength is attenuated by surface plasmon resonance is proposed, and a surface plasmon sensor basically constituted by a prism-shaped dielectric block, and a metal film formed on the block, and brought into contact with the specimen is disclosed, for example, in Japanese Unexamined Patent Publication No. 6 (1994)-167443. In the sensor, total reflection occurs at the interface between the dielectric block and the metal film. When testing a specimen, measuring light is irradiated on the sensor such that total reflection attenuation occurs by the surface plasmon resonance, and the intensity of the reflected light totally reflected at the interface is measured to detect the total reflection attenuation. In this way, measurement of the refractive index or density of the specimen, identification of the specimen, or the like is performed.

The plasmon sensor described above is expensive, since it requires the prism-shaped dielectric block. Further, it has many structural constraints, so that down-sizing of the sensor or simultaneous analysis of multiple specimens is difficult. Consequently, a different type of sensor that makes use of the phenomenon in which the light intensity of the reflected light having a particular wavelength is attenuated by local plasmon resonances is proposed, and a local plasmon sensor having microscopic metal relief structures on the surface of the substrate for effectively inducing local plasmon resonances is disclosed as described, for example, in Japanese Unexamined Patent Publication No. 2004-232027, or nonpatent literature, "Local plasmon sensor with gold colloid monolayers deposited upon glass substrates" by Takayuki Okamoto and Ichirou Yamaguchi, OPTICS LETTERS, Vol. 25, No. 6, pp 372-374, Mar. 15, 2000.

The local plasmon sensor described above has a simpler structure, and is less expensive with less structural constraints compared with the surface plasmon sensor, since no prism-shaped dielectric block is required. The local plasmon sensor, however, has less favorable detection sensitivity than the surface plasmon sensor so that accurate analysis is difficult.

DISCLOSURE OF INVENTION

The present invention has been developed in view of the circumstances described above, and it is an object of the present invention to provide a new and novel sensor having simpler structure with higher detection sensitivity than the surface plasmon sensor. It is a further object of the present invention to provide a sensing apparatus, and a sensing method using the same.

A sensor of the present invention is a sensor in which measuring light is inputted and outputted therefrom as output light after physical properties thereof are changed by a specimen, and detected, the sensor comprising the following arranged from input side of the measuring light in the order listed below:

a first reflector having semi-transmissive and semi-reflective properties;

a translucent body; and a second reflector having perfect reflection properties, or semi-transmissive and semi-reflective properties, wherein:

the first reflector and/or second reflector is brought into contact with the specimen, and the average complex refractive index thereof varies with the specimen;

absorption properties for absorbing light having a particular wavelength are produced according to the average complex refractive index of the first reflector, average complex refractive index of the second reflector, and average complex refractive index and thickness of the translucent body;

the properties of the measuring light are changed by the optical properties including the absorption properties, the output light is outputted from the first reflector and/or second reflector; and the physical properties of the output light that vary according to the optical properties are detected.

The referent of "semi-transmissive and semi-reflective properties" as used herein means having both translucency and reflectivity, and may have any transmittance and reflectance values.

Preferably, the first reflector and/or second reflector brought into contact with the specimen has a relief structure which is smaller than the wavelength of the measuring light.

The referent of "relief structure smaller than the wavelength of input light" as used herein means that the average size ("size" means the widest dimension) of the protruding portion and depressed portion ("depress portion" includes a space running through the reflector in the thickness direction), and the average pitch are smaller than the wavelength of the measuring light.

In the sensor according to a preferred embodiment, the first reflector and/or second reflector brought into contact with the specimen is constituted by a metal pattern layer made of a metal formed on the surface of the translucent body in a pattern.

In such embodiment, a sensor in which the properties of the measuring light are changed by the absorption properties and a local plasmon resonance may be provided.

In the sensor according to a further preferred embodiment, the first reflector and/or second reflector brought into contact with the specimen is constituted by a metal particle layer having a plurality of metal particles fixed on the surface of the translucent body.

In such embodiment, a sensor in which the properties of the measuring light are changed by the absorption properties and a local plasmon resonance on the metal particle layer may be provided.

In the sensor according to another preferred embodiment, a configuration is adopted in which:

the first reflector is brought into contact with the specimen, and the average complex refractive index thereof varies with the specimen;

the translucent body is constituted by a translucent porous body having a plurality of pores, each of which has a pore diameter substantially smaller than the wavelength of the measuring light and is open at the face on the side of the first reflector; and the first reflector is constituted by a metal layer having a plurality of pores formed along the surface contour of the translucent body.

In the sensor according to still another preferred embodiment, a configuration is adopted in which:

the first reflector is brought into contact with the specimen, and the average complex refractive index thereof varies with the specimen;

the translucent body is constituted by a translucent porous body having a plurality of pores, each of which has a pore diameter substantially smaller than the wavelength of the measuring light and is open at the face on the side of the first reflector;

the first reflector is constituted by a metal layer having a plurality of pores formed along the surface contour of the translucent body; and a metal is partially filled in each of the plurality of pores of the translucent body.

In such embodiment, a sensor in which the properties of the measuring light are changed by the absorption properties and a local plasmon resonance developed on at least one of the following: the first reflector, second reflector, and metal partially filled in each of the plurality of pores of the translucent body may be provided.

The absorption properties are produced by the optical interference effects. Therefore, the embodiment described above may provide a sensor in which the properties of the measuring light are changed by the absorption properties and a local plasmon resonance. Such sensor itself is new and novel, and included in the present invention.

A first multichannel sensor of the present invention is a sensor in which measuring light is inputted and outputted therefrom as output light after the physical properties thereof are changed by a plurality of specimens, and detected to allow simultaneous analysis of the plurality of specimens, S wherein:

the multichannel sensor includes one or more of any of the sensors of the present invention, which are divided into a plurality of sensor regions, each being brought into contact with each of the plurality of specimens; and the physical properties that vary according to the optical properties are detected with respect to each sensor region.

A second multichannel sensor of the present invention is a sensor in which measuring light is inputted and outputted therefrom as output light after the physical properties thereof are changed by a plurality of specimens, and detected to allow simultaneous analysis of the plurality of specimens, S wherein:

the multichannel sensor includes a plurality of any of the sensors of the present invention, and the physical properties that vary according to the optical properties are detected with respect to each sensor.

A sensor with specimen cell of the present invention is a sensor comprising:

any of the sensors of the present invention which is attached to a specimen cell fillable with the specimen, wherein the sensor is fixed to the specimen cell such that the first reflector and/or second reflector of the sensor is brought into contact with the specimen in the specimen cell.

A sensing apparatus of the present invention is an apparatus comprising:

any of the sensors or multichannel sensors of the present invention;

a measuring light irradiation means for irradiating the measuring light on the sensor or multichannel sensor; and a detection means for detecting the physical properties of the output light.

Preferably, the detection means is constructed to detect at least one of the following: the light intensity of the output light, variation thereof, absorption peak wavelength of light absorbed by the sensor, and the amount of shift thereof.

The sensing apparatus of the present invention may analyze the refractive index and/or density of the specimen. Further, it may identify the specimen by analyzing the refractive index thereof.

A sensing method of the present invention is a method using any of the sensors or multichannel sensors of the present invention, the method comprising the steps of:

fixing a binding substance that specifically combines with a particular substance on the side of the sensor S or multichannel sensor MS to be brought into contact with the specimen before bringing the specimen into contact therewith;

irradiating the measuring light on the sensor or multichannel sensor; and detecting the physical properties of the output light to analyze the presence of the particular substance and/or amount thereof in the specimen.

In the sensor of the present invention, a configuration is adopted in which the following is arranged from input side of the measuring light in the order listed below: a first reflector having semi-transmissive and semi-reflective properties; a translucent body; and a second reflector having perfect reflection properties, or semi-transmissive and semi-reflective properties.

In such structure, the light transmitted through the first reflector and entered into the translucent body repeats reflections between the first reflector and second reflector, causing multipath reflection (resonance) to occur effectively. Thereby, multipath reflection interference is developed effectively. In the sensor of the present invention, the multipath interference conditions vary according to the average complex refractive index of the first reflector, average complex refractive index of the second reflector, and average complex refractive index and thickness of the translucent body. Therefore, the absorption properties for absorbing light having a particular wavelength are produced according to these factors, and output light having physical properties which differ from those of the measuring light according to the absorption properties is outputted from the first reflector and/or second reflector.

In the sensor of the present invention, a configuration is adopted in which the first reflector and/or second reflector is brought into contact with the specimen, and the average complex refractive index thereof varies with the specimen. In such structure, the multipath interference conditions, hence the absorption properties are changed by the specimen. Therefore, specimen analysis may be performed by detecting the physical properties of the output light that vary according to the absorption properties.

In the sensor of the present invention, a configuration is adopted in which a translucent body is sandwiched by two different reflectors, which is much simpler with less expensive and less structural constraints compared with the surface plasmon sensor.

In the sensor of the present invention, multipath interference occurs effectively, and light having a particular wavelength is strongly absorbed. Consequently, the sensor of the present invention has higher detection sensitivity compared with the conventional local plasmon sensor, and allows highly accurate analysis.

BRIEF DESCRIPTION OF DRAWINGS

FIG. 8A is a schematic cross-sectional view of the sensor with specimen cell according to an embodiment of the present invention, illustrating the structure thereof.

FIG. 8B is a drawing illustrating an example of design change of the sensor with specimen cell.

FIG. 9A is a block diagram of the sensing apparatus according to a first embodiment of the present invention, illustrating the structure thereof.

FIG. 9B is a block diagram of the sensing apparatus according to a second embodiment of the present invention, illustrating the structure thereof.

FIG. 9C is a block diagram of the sensing apparatus according to a third embodiment of the present invention, illustrating the structure thereof.

BEST MODE FOR CARRYING OUT THE INVENTION

First Embodiment of the Sensor

Figure 1A:
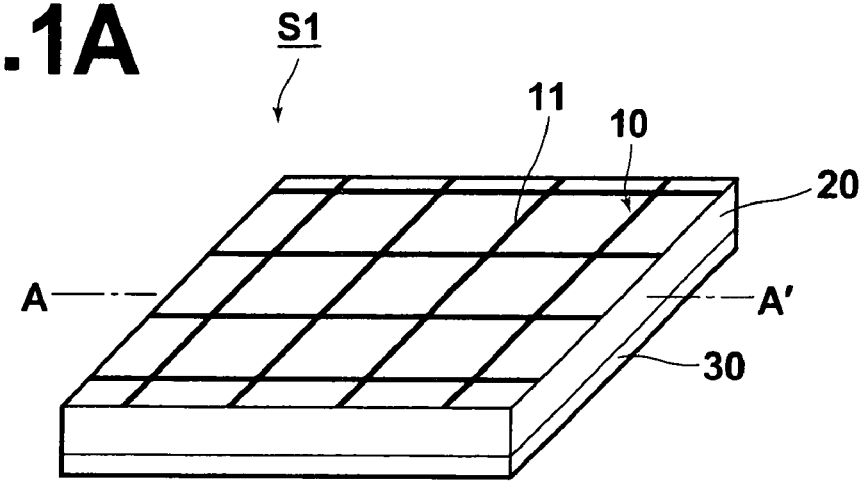
FIG. 1A is a perspective view of the sensor according to a first embodiment of the present invention.

Hereinafter, the sensor according to a first embodiment of the present invention will be described with reference to FIGS. 1A, 1B, 1C. FIG. 1A is a perspective view, FIG. 1B is a cross-sectional view in thickness direction (taken along the line A-A in FIG. 1), and FIG. 1C is a drawing illustrating example spectra of the output light of the sensor.

Figure 1B:
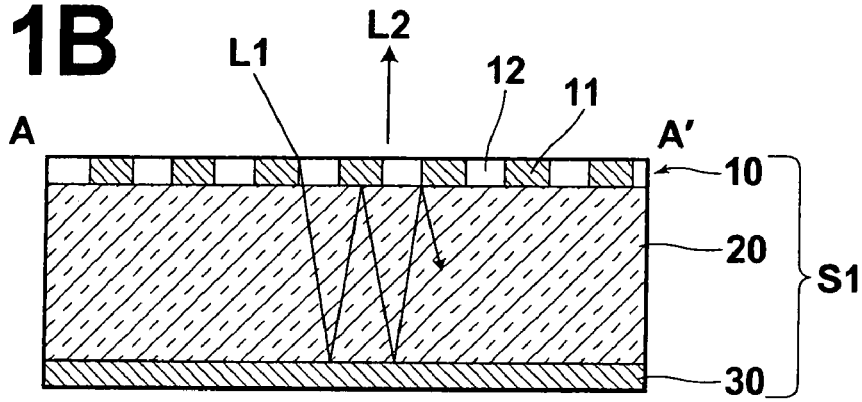
FIG. 1B is a cross-sectional view in thickness direction of the sensor shown in FIG. 1A.
Figure 1C:
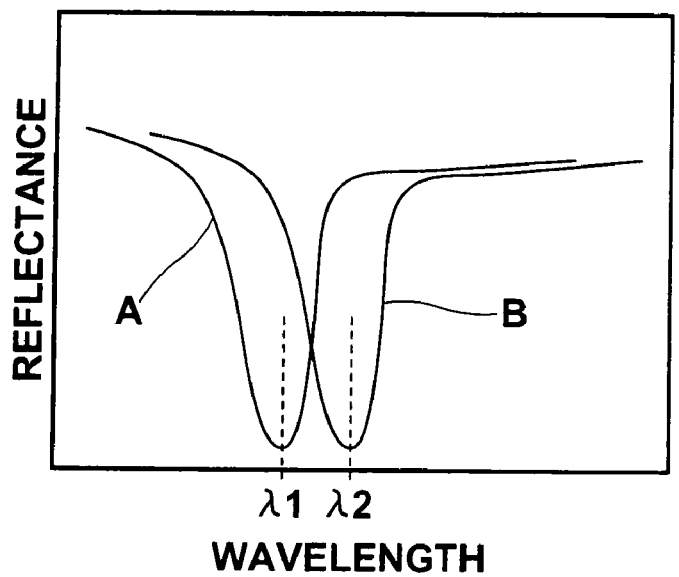
FIG. 1C is a drawing illustrating example spectra of the output light of the sensor shown in FIG. 1A.

As shown in FIGS. 1A, 1B, the sensor S1 of the present embodiment has a device structure in which the following components are arranged from the input side of the measuring light L1 (upper side in FIG. 1B) in the order listed below: a first reflector 10 having semi-transmissive and semi-reflective properties; a translucent body 20; and a second reflector 30 having perfect reflection properties. Either single wavelength light or broad light may be used as the measuring light L1, which is selected according to the physical properties to be detected.

The translucent body 20 is constituted by a translucent planar substrate, the first reflector 10 is constituted by a metal pattern layer having thin metal wires 11 formed in a regular lattice pattern provided on one surface of the translucent body 20, and the second reflector 30 is constituted by a sold metal layer provided on the other surface of the translucent body 20.

There is no specific limitation on the material of the translucent body 20, and glass, translucent ceramic, such as alumina, and translucent resin, such as acrylic resin, carbonate resin, and the like may be used.

Any reflective metals may be use for the first reflector 10 and the second reflector 30, which include Au, Ag, Cu, Al, Pt, Ni, Ti, alloys of these, and the like. The first reflector 10 and the second reflector 30 may include two or more different metals.

The second reflector 30, which is a solid metal layer, may be formed, for example, by metal vapor deposition or the like. The first reflector 10 may be formed, for example, by first forming a solid metal layer by metal vapor deposition or the like, then performing the known method of photolithography on the metal layer.

Although the first reflector 10 is made of a reflective metal, it has a plurality of pattern spaces which are translucent empty spaces, so that it has semi-transmissive and semi-reflective properties. The line width and the pitch of the thin metal wires 11 of the first reflector 10 are designed smaller than the wavelength of the measuring light L1. Consequently, it has relief structures smaller than the wavelength of the measuring light L1. The first reflector 10 having such relief structures acts as a semi-transmissive and semi-reflective thin film for light due to what is known as the electromagnetic mesh shielding effects.

In the sensor S1 according to the present embodiment, each of the first reflector 10 and the second reflector 30 is a sensing body that varies its complex refractive index according to the specimen brought into contact therewith. Thus, the analysis of a specimen may be performed by brining the specimen into contact with the first reflector 10 and/or second reflector 30.

In particular, the first reflector 10 has relief structures smaller than the wavelength of the measuring light L1 constituted by the thin metal wires 11 and pattern spaces 12, so that the variation in the complex refractive index of the reflector 10 caused by the specimen is more significant. This is because, it is thought, the oscillation of the measuring light L1 or the like is effectively induced by the relief structures of the first reflector 10. Accordingly, it is preferable that the analysis of a specimen is performed by bringing the specimen into contact at least with the side of the first reflector 10.

There is no specific limitation on the pitch of the thin metal wire 11 as long as it is smaller than the wavelength of the measuring light L1. If visible light is used as the measuring light L1, the pitch is preferable, for example, less than or equal to 200 nm. A narrower pitch for the thin metal wires 11 is preferable in view of the sensitivity.

There is no specific limitation on the line width of the thin metal wire 11, but the smaller width is preferable in view of the sensitivity. Preferably, the line width of the thin metal wire 11 is smaller than or equal to the mean free path of the electrons oscillating in the metal. More specifically, it is preferable to be less than or equal to 50 nm, and more preferable to be less than or equal to 30 nm.

Smaller pitch and line width of the thin metal wire 11 result in larger proportion of the surface area relative to a single thin metal wire 11. Consequently, surface characteristic of the thin metal wires 11 is more likely to be reflected in the overall characteristics of the reflector 10, and thereby high sensitivity may be obtained. More specifically, smaller pitch and line width of the thin metal wires 11 result in a larger variation in the dielectric constant of the first reflector 10 arising from different specimens, which causes a larger variation in the average complex refractive index (effective complex refractive index) of the first reflector 10, and thereby high sensitivity may be obtained.

As shown in FIG. 1B, when the measuring light L1 is incident on the sensor S1, a portion of the light is reflected at the surface of the first reflector 10 (not shown) and the other portion of the light transmits through the first reflector 10 and enters into the translucent body 20 in accordance with the transmittance and reflectance of the first reflector 10. The light entered into the translucent body 20 repeats reflections between the first reflector 10 and second reflector 30. That is, the Sensor S1 has a resonance structure in which multipath reflection occurs between the first reflector 10 and the second reflector 30.

In such device, multipath reflection interference occurs, and absorption properties for selectively absorbing light having a particular wavelength are produced. The multipath interference conditions depend on the average complex refractive index of the first reflector 10, average complex refractive index of the second reflector 30, and average complex refractive index and thickness of the translucent body 20. Therefore, light having a particular wavelength is absorbed according to these factors, and the output light L2 having physical properties which differ from those of the measuring light L1 according to the absorption properties is outputted. The sensor S1 of the present embodiment is a reflective type sensor in which the output light L2 is outputted only from the first reflector 10, since the second reflector 30 has perfect reflection properties.

Here an assumption is made in which average complex refractive index of the first reflector 10 is $n_1-ik_1$, average complex refractive index of the translucent body 20 is $n_2$, average complex refractive index of the second reflector 30 is $n_3-ik_3$, and thickness of the translucent body 20 is d. (where, $k_1, k_2$ are extinction coefficients, $-ik_1$ and $-ik_3$ indicate imaginary parts, and the imaginary part of the complex refractive index of the translucent body 20 is zero in the present embodiment).

The inventors of the present invention have found that the peak wavelength (absorption peak wavelength) $\lambda$ of light absorbed by the multipath interference depends largely on the average complex refractive index $n_2$ and thickness d of the translucent body 20 when the measuring light L1 is substantially normal incident light, and is basically expressed by the following formula. That is, the inventors of the present invention have found that the absorption peak wavelength $\lambda$ appears near the wavelength expressed by the following formula, which varies around the wavelength expressed by the following formula according to the average complex refractive index $n_1-ik_1$ of the first reflector 10, average complex refractive index $n_3-ik_3$ of the second reflector 30, and the average complex refractive index $n_2$ and thickness d of the translucent body 20.

$$n_2 d \approx (m+1)/2 \times \lambda$$

$$\lambda \approx (m+1) \times 2 n_2 d$$

where, m is an arbitrary integer value (0, ±1, ±2, or the like).

In particular, if at least any of the reflector 10, translucent body 20, or second reflector 30 is constituted by a light absorption body with the imaginary part of the complex dielectric constant thereof is other than zero, then a sharp absorption peak is obtained, that is, strong absorption properties for absorbing light having a particular wavelength may be produced. In the present embodiment, the first reflector 10 and the second reflector 30, which are metal layers, are light absorption bodies with the imaginary part of the complex dielectric constant thereof is other than zero.

There is no specific limitation on the thickness d of the translucent body 20. Preferably, however, the thickness d is, for example, not greater than 300 nm, in which case only a single absorption peak wavelength due to multipath interference appears in the visible light wavelength range and the detection thereof is facilitated. Further, the thickness d of the translucent body 20 is preferable not to be less than 100 nm, in which case multipath reflection occurs effectively and the absorption peak wavelength due to multipath interference appears in the visible light range and the detection thereof is facilitated.

Preferably, the sensor S1 has a device structure in which the optical impedance is matched to maximize the number of multipath reflection times (finesse). Such structure may produce a sharp absorption peak, and allows more accurate analysis.

When a specimen is brought into contact with the first reflector 10 and/or second reflector 30 (preferably with the first reflector 10), the average complex refractive index (effective complex refractive index) of the reflector brought into contact with the specimen varies through the interaction between the reflector and specimen, thereby the multipath interference conditions are changed. That is, the absorption properties due to the multipath interference are changed.

Examples of the reflected light spectra (examples of the output light spectra) obtained by irradiating white light as the measuring light L1, and bringing different specimens A and B into contact with the first reflector 10 are shown in FIG. 1C. FIG. 1C illustrates that the absorption peak wavelength $\lambda$ varies from $\lambda 1$ to $\lambda 2$ by changing the specimens.

In the sensor S1, the analysis of the specimen may be performed by detecting the physical properties of the output light L2 that vary according to the absorption properties. The physical properties of the output light L2 that vary according to the absorption properties include the light intensity of the output light L2 or variation thereof, absorption wavelength of the light absorbed by the sensor S1 or the amount of shift thereof, and the like. Specific examples of the structure of the sensing apparatus will be described later.

The sensor S1 of the present embodiment may analyze refractive index and/or density of a specimen. It may also identify the specimen by analyzing the refractive index thereof. Further, it may also analyze presence of a particular substance in the specimen and/or the amount thereof by fixing a binding substance that specifically combines with the particular substance on the reflector to be brought into contact with the specimen (first reflector 10 and/or second reflector)

before bringing the specimen into contact therewith, and irradiating the measuring light L1 on the sensor S1 and detecting the output light L2. Combinations of the particular substance and binding substance may include the combination of antigen and antibody (either may be the binding substance) and the like, and the present embodiment may also perform time-course analysis of antigen-antibody reactions and the like.

The sensor S1 according to the present embodiment is structured in the manner as described above.

That is, the sensor S1 according to the present embodiment has a device structure that includes the following arranged from the input side of the measuring light L1 in the order listed below: the first reflector 10 having semi-transmissive and semi-reflective properties; translucent body 20; and second reflector 30 having perfect reflection properties.

In such structure, the light transmitted through the first reflector 10 and entered into the translucent body 20 repeats reflections between the first reflector 10 and second reflector 30, causing multipath reflection (resonance) to occur effectively. Thereby, multipath reflection interference is developed effectively. In the sensor S1 according to the present embodiment, the multipath interference conditions vary according to the average complex refractive index of the first reflector 10, average complex refractive index of the second reflector 30, and average complex refractive index and thickness of the translucent body 20. Therefore, the absorption properties for absorbing light having a particular wavelength are produced according to these factors, and output light L2 having physical properties which differ from those of the measuring light L1 according to the absorption properties is outputted from the first reflector 10.

In the sensor S1 according to the present embodiment, the first reflector 10 and/or second reflector 30 is brought into contact with a specimen, and average complex refractive index thereof varies with the specimen. In such structure, the multipath interference condition varies with the specimen, and thereby absorption properties are changed. Thus, analysis of the specimen may be performed by detecting the physical properties of the output light L2 that vary according to the absorption properties.

The sensor S1 according to the present embodiment has a device structure in which the translucent body 20 is sandwiched by the two reflectors 10, 30, which is much simpler than the surface plasmon sensor with less expensive and less structural constraints.

In the sensor S1 according to the present embodiment, the multipath interference occurs effectively and strong absorption properties for absorbing light having a particular wavelength are produced. Thus, it has higher detection sensitivity than the conventional local plasmon sensor, and allows highly accurate analysis.

Further, the sensor S1 according to the present embodiment may cause local plasmon resonances to occur effectively on the surface of the first reflector 10 constituted by a metal pattern layer.

The local plasmon resonance is a phenomenon in which an electric field is developed by the oscillation of free electrons in a metal in resonance with a light electric field. It is thought that in a metal layer having relief structures, in particular, strong electric fields are developed around protruding portions by the oscillation of free electrons of the protruding portions in resonance with electric fields of light, causing local plasmon resonances to occur effectively. In the present embodiment, the first reflector 10 has relief structures smaller than the wavelength of the measuring light L1, so that local plasmon resonances occur effectively.

For the wavelength at which the local plasmon resonance occurs, the scattering and absorption of the measuring light L1 are increased significantly, and the intensity of the reflected light having such wavelength decreases remarkably. The optical wavelength that causes the plasmon resonance (resonance peak wavelength), and the extent of the scattering and absorption of the measuring light L1 depend on the refractive index of the specimen placed on the surface of the sensor S1 and the like.

The present embodiment may provide a sensor in which the properties of the measuring light L1 are changed by absorption properties due to the optical interference effects described above, and the local plasmon resonances on the first reflector 10. In such sensor, the analysis of a specimen may be performed by detecting both physical properties 1 of the measuring light L2 that vary according to the absorption properties due to the optical interference effects, and physical properties 2 of the measuring light L2 that vary according to the local plasmon resonances. Further, it may analyze the specimen by detecting the correlation between the physical properties 1 and physical properties 2.

Normally, the absorption peak caused by the multipath interference and the absorption peak caused by the local plasmon resonances appears at different wavelengths. Thus, the sensor S1 according to the present embodiment allows more accurate analysis by detecting each of the physical changes caused by the multipath interference and local plasmon resonances. In FIG. 1C, the absorption peak caused by the local plasmon resonances is omitted. The absorption peak caused by the multipath interference and the absorption peak caused by the local plasmon resonances may sometimes overlap with each other.

As for the material of the first reflector 10 and second reflector 30, a metal is preferable since it allows sensing based on the local plasmon resonances as well, but a non-metal reflective material may also be used.

In the present embodiment, description has been made that the first reflector 10 has a regular lattice pattern as an example. But the first reflector 10 may have any pattern including a random pattern. But high structural regularity is preferable in view of the sensitivity, since higher structural regularity provides higher in-plane uniformity and more consolidated properties.

Second Embodiment of the Sensor

Figure 2A:
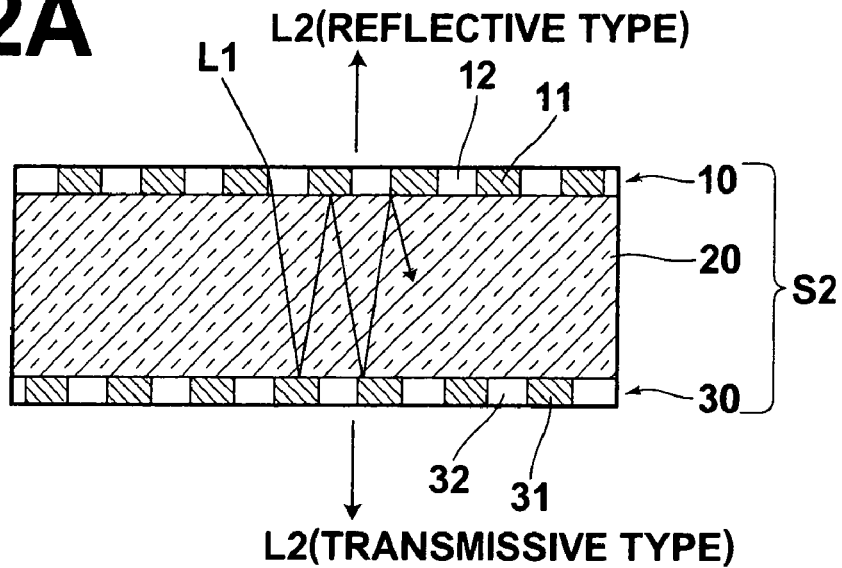
FIG. 2A is a cross-sectional view in thickness direction of the sensor according to a second embodiment.
Figure 2B:
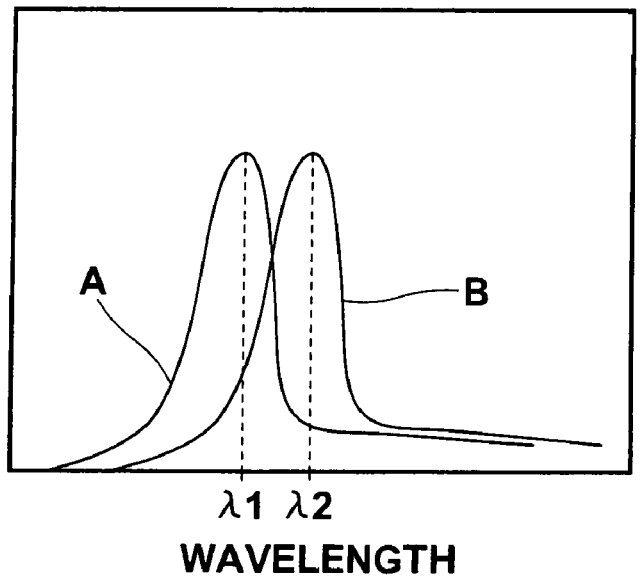
FIG. 2B is a drawing illustrating example spectra of the output light of the sensor shown in FIG. 2A.

Hereinafter, the sensor according to a second embodiment of the present invention will be described with reference to FIGS. 2A and 2B. FIG. 2A is a cross-section view corresponding to FIG. 1B of the first embodiment. FIG. 2B shows example spectra of the output light. In the present embodiment, components identical to those of the first embodiment are given the same reference symbols and will not be elaborated upon further here.

As shown in FIG. 2A, the sensor S2 according to the present embodiment has a device structure that includes the following arranged from the input side of the measuring light L1 in the order listed below: the first reflector 10; translucent body 20; and second reflector 30 as in the first embodiment. The present embodiment differs from the first embodiment in that the second reflector 30 is constituted by a metal pattern layer having thin metal wires 31 formed in a regular lattice pattern as in the first reflector 10, and has semi-transmissive and semi-reflective properties, while in the first embodiment, the second reflector is constituted by a solid metal layer, and has perfect reflection properties (perspective view of the second reflector 30 is identical to the first reflector 10 in FIG. 1A).

In the sensor S2 according to the present embodiment, each of the first reflector 10 and the second reflector 30 is a sensing body that varies its complex refractive index according to the specimen brought into contact therewith. Thus, the analysis of a specimen may be performed by brining the specimen into contact with the first reflector 10 and/or second reflector 30. In the present embodiment, each of the first reflector 10 and second reflector 30 has relief structures smaller than the wavelength of the measuring light L1. Thus, bringing a specimen into contact with either of the reflectors may result in high sensitivity variation to occur in the average complex refraction index of the reflector caused by the specimen.

Also in the present embodiment, multipath reflection (resonance) occurs effectively between the first reflector 10 and the second reflector 30 as in the first embodiment. Thereby multipath reflection interference occurs effectively, and the absorption properties for absorbing light having a particular wavelength are produced. When a specimen is brought into contact with the first reflector 10 and/or second reflector 30, the average complex refractive index (effective complex refractive index) of the reflector brought into contact with the specimen is changed. That is, the multipath interference conditions, hence the absorption properties vary with the specimen. Thus, when the second reflector 30 is semi-transmissive and semi-reflective, the analysis of the specimen may be performed by detecting the physical properties of the output light L2 that vary according to the absorption properties.

Whereas in the first embodiment in which the second reflector 30 has perfect reflection properties, only a reflective type sensor is provided, in the present embodiment in which the second reflector 30 has semi-transmissive and semi-reflective properties, any of the following may be provided: the reflective type sensor in which the output light L2 is outputted only from the first reflector 10, transmissive type reflector in which the output light L2 is outputted only from the second reflector 30, or semi-transmissive and semi-reflective type sensor in which the output light L2 is outputted from both the first reflector 10 and second reflector 30 according to average complex refractive index of the first reflector 10, average complex refractive index of the second reflector 30, and average complex refractive index and thickness of the translucent body 20.

In the reflective type sensor or semi-transmissive and semi-reflective type sensor, example spectra of the output light L2 (reflected light) outputted from the first reflector 10 are identical to those shown in the first embodiment. FIG. 2B shows example spectra of the output light L2 (transmitted light) outputted from the second reflector 30 in the transmissive type sensor or semi-transmissive and semi-reflective type sensor. FIG. 2B shows absorption spectra, and illustrates that the absorption peak wavelength λ varies from λ1 to λ2 by changing the specimens.

In the sensor S2 according to the present embodiment, each of the first reflector 10 and second reflector 30 is constituted by a metal pattern layer, so that local plasmon resonances may be caused to occur effectively on the surface of the first reflector 10 and/or second reflector 30. Accordingly, the present embodiment may provide a sensor in which the properties of the measuring light L1 are changed by absorption properties due to the optical interference effects described above, and the local plasmon resonances on the first reflector 10 and/or second reflector 30. In such sensor, the analysis of a specimen may be performed by detecting both physical properties 1 of the measuring light L2 that vary according to the absorption properties due to the optical interference effects, and a physical properties 2 of the measuring light L2 that vary according to the local plasmon resonances. Further, it may analyze the specimen by detecting the correlation between the physical properties 1 and physical properties 2.

The sensor S2 according to the present embodiment is structured in the manner as described above. That is, the basic structure of the present embodiment is identical to that of the first embodiment, except that the second reflector 30 has semi-transmissive and semi-reflective properties. Therefore, the present embodiment may provide similar advantageous effects to those of the first embodiment. In the present embodiment, description has been made in which the first reflector 10 and second reflector 30 have the identical pattern, but they may have different patterns.

Third Embodiment of the Sensor

Figure 3A:
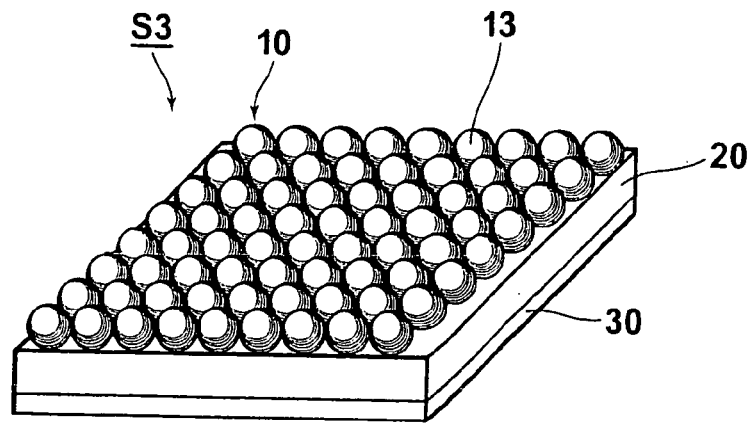
FIG. 3A is a cross-sectional view in thickness direction of the sensor according to a third embodiment.
Figure 3B:
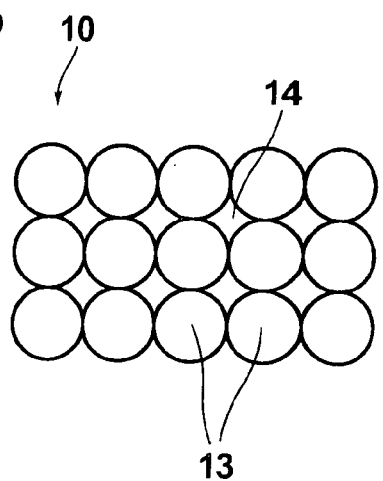
FIG. 3B is a top view of the sensor shown in FIG. 3A.

Hereinafter, the sensor according to a third embodiment of the present invention will be described with reference to FIGS. 3A and 3B. FIG. 3A is a perspective view corresponding to FIG. 1A of the first embodiment. FIG. 3 is a top view of the sensor. In the present embodiment, components identical to those of the first embodiment are given the same reference symbols and will not be elaborated upon further here.

As shown in FIG. 3A, the sensor S3 according to the present embodiment has a device structure that includes the following arranged from the input side of the measuring light L1 in the order listed below: the first reflector 10 having semi-transmissive and semi-reflective properties; translucent body 20; and second reflector 30 having perfect reflection properties as in the first embodiment.

The present embodiment differs from the first embodiment in that the first reflector 10 is constituted by a metal particle layer having a plurality of metal particles 13 with substantially the same diameter arranged regularly in a matrix and fixed on the surface of the translucent body 20, while in the first embodiment, the first reflector 10 is a patterned metal layer. There is no specific limitation on the material of the metal particle, and metals identical to those described in the first embodiment may be used.

The first reflector 10 described above may be formed, for example, by applying a solution with the metal particles 13 dispersed therein on the surface of the translucent body by spin coating and drying. Preferably, the solution includes a binder such as a resin, protein, or the like, to fix the metal particles 13 on the surface of the translucent body 20 through the binder. When protein is used as the binder, binding reaction of the protein may be used to fix the metal particles 13 on the surface of the translucent body 20.

Although the first reflector 10 is made of a reflective metal, it has a plurality of particle spaces 14 which are translucent empty spaces, so that it has semi-transmissive and semi-reflective properties. The diameter and pitch of the metal particles 13 are designed smaller than the wavelength of the measuring light L1. Consequently, it has relief structures smaller than the wavelength of the measuring light L1. Also in the present embodiment, the first reflector 10 acts as a semi-transmissive and semi-reflective thin film for light due to what is known as the electromagnetic mesh shielding effects.

Also in the sensor 3 according to the present embodiment, each of the first reflector 10 and the second reflector 30 is a sensing body that varies its complex refractive index according to the specimen brought into contact therewith. Thus, the analysis of a specimen may be performed by brining the specimen into contact with the first reflector 10 and/or second reflector 30.

In particular, the first reflector 10 has relief structures smaller than the wavelength of the measuring light L1 constituted by the metal particles 13 and particle spaces 14, so that the variation in the complex refractive index of the reflector 10 caused by the specimen is more significant due to the same reason as describe in the first embodiment. Accordingly, it is preferable that the analysis of the specimen is performed by bringing the specimen into contact at least with the side of the first reflector 10.

There is no specific limitation on the pitch of the metal particle 13 as long as it is smaller than the wavelength of the measuring light L1. If visible light is used as the measuring light L1, the pitch is preferable, for example, less than or equal to 200 nm. A narrower pitch for the metal particles is preferable in view of the sensitivity.

There is no specific limitation on the diameter of the metal particles 13, but the smaller diameter is preferable in view of the sensitivity. Preferably, the diameter of the metal particles 13 is smaller than or equal to the mean free path of the electrons oscillating in the metal. More specifically, it is preferable to be less than or equal to 50 nm, and more preferable to be less than or equal to 30 nm.

As in the metal thin wires 11 of the first embodiment, smaller pitch and diameter of the metal particles 13 result in larger proportion of the surface area relative to a single metal particle 13. Consequently, surface characteristic of the metal particles 13 is more likely to be reflected in the overall characteristics of the reflector 10, and thereby high sensitivity may be obtained.

In the present embodiment, as in the first embodiment, light reflections are repeated between the first reflector 10 and the second reflector 30, causing multipath reflection (resonance) to occur effectively. This causes multipath reflection interference to be developed effectively, and the absorption properties for absorbing light having a particular wavelength are produced. Also in the present embodiment, average complex refractive index (effective complex refractive index) of the first reflector 10 and/or second reflector 30 varies with the specimen. That is, the multipath interference conditions, hence the absorption properties vary with the specimen. Thus, the analysis of the specimen may be performed in the same manner as in the first embodiment.

The sensor S3 according to the present embodiment may cause local plasmon resonances to occur effectively on the surface of the first reflector 10 constituted by the metal particle layer. Accordingly, the present embodiment may provide a sensor in which the properties of the measuring light L1 are changed by absorption properties due to the optical interference effects described above, and the local plasmon resonances on the first reflector 10 as in the first embodiment. In such sensor, the analysis of a specimen may be performed by detecting both physical properties 1 of the measuring light L2 that vary according to the absorption properties due to the optical interference effects, and physical properties 2 of the measuring light L2 that vary according to the local plasmon resonances. Further, it may analyze the specimen by detecting the correlation between the physical properties 1 and physical properties 2.

The sensor S3 according to the present embodiment is structured in the manner as described above.

That is, the basic structure of the present embodiment is identical to that of the first embodiment, except that the first reflector 10 is constituted by the metal particle layer. Therefore, the present embodiment may provide similar advantageous effects to those of the first embodiment.

In the present embodiment, description has been made in which the first reflector 10 is constituted by a metal layer having a plurality of metal particles 13 with substantially the same diameter arranged regularly in a matrix and fixed on the surface of the translucent body 20 as an example. But the metal particles 13 may have different diameters, and they may be arranged any pattern including a random pattern. Further, description has been made in which the second reflector 30 is constituted by the solid metal layer. But the second reflector may also be constituted by a metal particle layer as in the first reflector 10. In this case, the second reflector 30 has semi-transmissive and semi-reflective properties, and the analysis of a specimen may be performed in the same manner as in the second embodiment.

Fourth Embodiment of the Sensor

Figure 4:
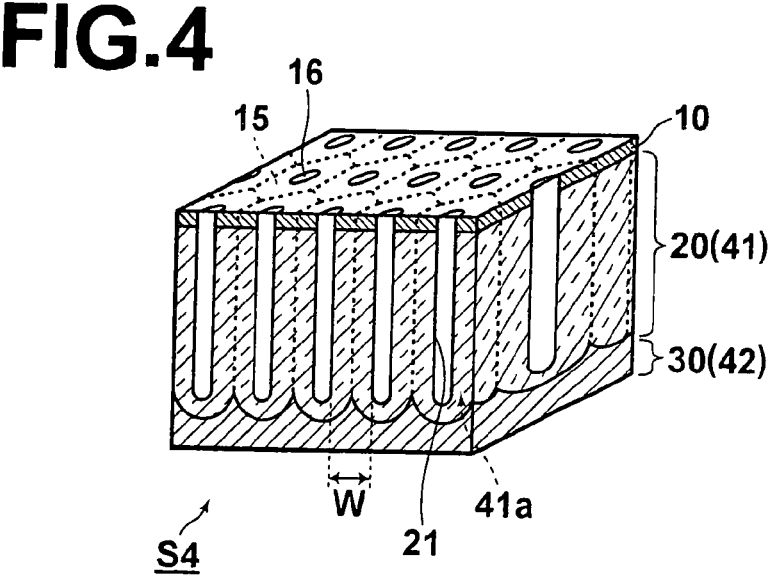
FIG. 4 is a perspective view of the sensor according to a fourth embodiment of the present invention.
Figure 5A:
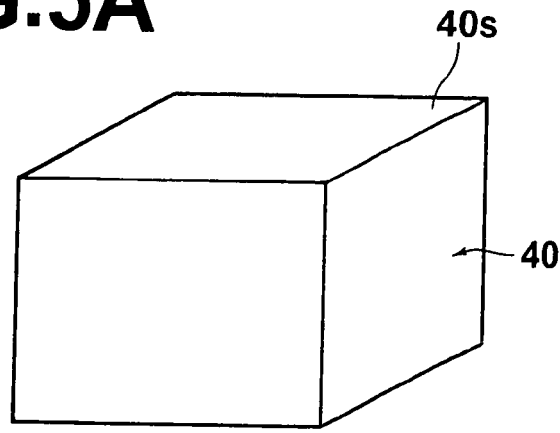
FIGS. 5A to 5C are drawings illustrating the manufacturing process of the sensor shown in FIG. 4.
Figure 5B:
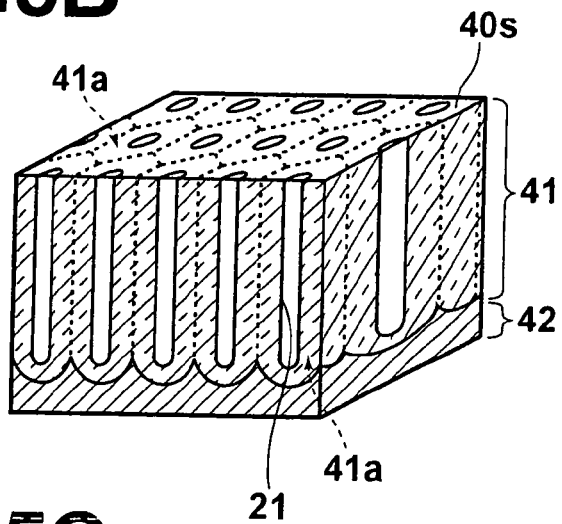
Figure 5C:
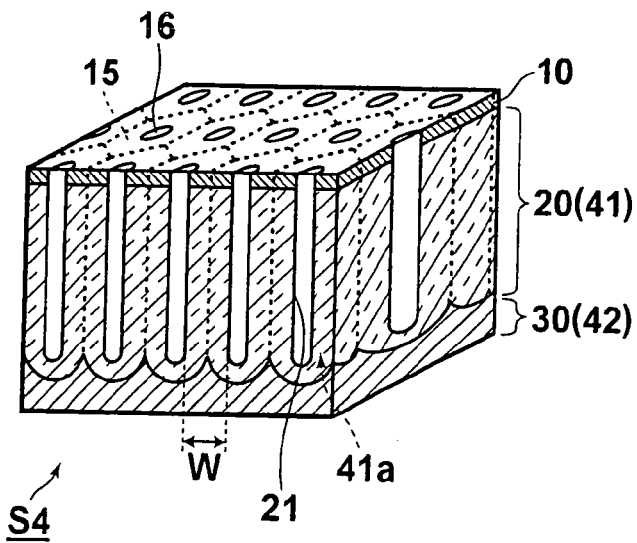

Hereinafter, the sensor according to a fourth embodiment of the present invention will be described with reference to FIGS. 4 and 5A to 5C. FIG. 4 is a perspective view of the sensor. FIGS. 5A to 5C are drawings illustrating the manufacturing process thereof. In the present embodiment, components identical to those of the first embodiment are given the same reference symbols and will not be elaborated upon further here.

As shown in FIG. 4, the sensor 4 according to the present embodiment has a device structure that includes the following arranged from the input side of the measuring light L1 in the order listed below: the first reflector 10 having semi-transmissive and semi-reflective properties; translucent body 20; and second reflector 30 having perfect reflection properties as in the first embodiment.

Unlike the first embodiment, in the present embodiment, the translucent body 20 is constituted by a metal oxide body ($Al_2O_3$) 41 obtained by anodizing a portion of an anodizable metal body (Al) 40 shown in FIG. 5B, and the second reflector 30 is constituted by the non-anodized portion (Al) 42 of the anodizable metal body 40 shown in FIG. 5B. The second reflector 30 has perfect reflection properties.

The translucent body 20 is a translucent porous body having a plurality of pores formed therein that extends from the side of the first reflector 10 toward the side of the second reflector 30. The plurality of the pores is open at the face on the side of the first reflector 10 and closed on the side of the second reflector 30. In the translucent body 20, the plurality of pores 21 is arranged substantially regularly with a diameter and pitch smaller than the wavelength of the measuring light L1.

Anodization is implemented by immersing the anodizable metal body 40 together with cathode in an electrolyte solution with the metal body 40 as anode, and applying a voltage between the anode and cathode. There is no specific limitation on the geometry of the anodizable metal body 40, but a plate-like shape or the like is preferable. Further, the metal body 40 may include a base, on which anodizable metal is formed as a layer or the like. Carbon or aluminum is used as the cathode. There is no specific limitation on the type of the electrolyte solution, and an acid electrolyte solution that contains one or more acids selected from the group consisting of sulfuric acid, phosphoric acid, chromium acid, oxalic acid, sulfamic acid, benzenesulfonic acid, amidosulfonic acid, and the like is preferably used.

As shown in FIGS. 5A and 5B, when the anodizable metal body 40 is anodized, oxidizing reaction proceeds from the surface 40s in the direction substantially perpendicular to the surface 40s, and the metal oxide body ($Al_2O_3$) 41 is formed. The metal oxide body 41 formed by the anodization has a structure that includes a multitude of fine column bodies 41a disposed without any gap with substantially a hexagonal shape when viewed from above. Each of the pores 21 extending substantially linearly in the depth direction from the surface 40s is formed at the approximate center of each of the column bodies 41a, and the bottom of each of the column bodies 41a has a rounded surface. The structure of a metal oxide body formed by the anodization is described, for example, in Material Technology Vol. 15, No. 10, p 34, 1997.

Preferable examples of the anodization conditions when oxalic acid is used as the electrolyte solution includes: electrolyte solution density of 0.5M; solution temperature from 14 to 16 degrees Celsius; and application voltage of 40±0.5V. The pores 21 formed under these conditions have, for example, a pore diameter of 5 to 200 nm with a pitch of 10 to 400 nm.

In the present embodiment, the first reflector 10 is constituted by a metal layer formed along the surface contour of the translucent body 20 by metal vapor deposition or the like. Since no metal is formed on the aperture areas of the pores 21 of the translucent body 20, so that the first reflector 10 has substantially hexagonal metal bodies 15, each having a pore 16 at the approximate center thereof, disposed without any gap when viewed from above. The pores 16 of the first reflector 10 are formed in the same pattern as the pores 21 of the translucent body 20, so that the pores 16 are arranged substantially regularly with a diameter and pitch smaller than the wavelength of the measuring light L1.

The first reflector 10 is made of a reflective metal, but has a plurality of pores 16 which are translucent empty spaces, so that it has semi-transmissive and semi-reflective properties. The first reflector 10 is constituted by substantially hexagonal metal bodies 15, each having a pore 16 at the approximate center thereof, disposed substantially regularly without any gap when viewed from above, so that it has relief structures smaller than the wavelength of the measuring light L1. Also in the present embodiment, the first reflector 10 acts as a semi-transmissive and semi-reflective thin film for light due to what is known as the electromagnetic mesh shielding effects.

In the sensor 4 according to the present embodiment, each of the first reflector 10 and the second reflector 30 is a sensing body that varies its complex refractive index according to the specimen brought into contact therewith. Thus, the analysis of a specimen may be performed by brining the specimen into contact with the first reflector 10 and/or second reflector 30.

In particular, the first reflector 10 has relief structures smaller than the wavelength of the measuring light L1 constituted by the substantially hexagonal metal bodies 15 when view from above and pores 16, so that the variation in the complex refractive index of the reflector 10 caused by the specimen is more significant by the same reason as described in the first embodiment. Accordingly, it is preferable that the analysis of the specimen is performed by bringing the specimen into contact at least with the side of the first reflector 10.

There is no specific limitation on the pitch of the metal body 15 (pitch of the pore 16), as long as it is smaller than the wavelength of the measuring light L1. If visible light is used as the measuring light L1, the pitch is preferable, for example, less than or equal to 200 nm. A narrower pitch for the metal body 15 is preferable in view of the sensitivity.

There is no specific limitation on the distance between the adjacent pores 16 (width W of the metal body 15 between the adjacent pores 16), but smaller distance is preferable in view of the sensitivity. The width W corresponds to the width of the thin metal wire of the first embodiment, and the diameter of the metal particle 13 of the third embodiment. Preferably, the width W is smaller than or equal to the mean free path of the electrons oscillating in the metal. More specifically, it is preferable to be less than or equal to 50 nm, and more preferable to be less than or equal to 30 nm.

As in the thin metal wire 11 of the first embodiment, smaller pitch and width W of the metal body 15 allow surface characteristic of the metal body 15 to be more likely reflected in the overall characteristics of the reflector 10, and thereby high sensitivity may be obtained.

In the present embodiment, as in the first embodiment, light reflections are repeated between the first reflector 10 and the second reflector 30, causing multipath reflection (resonance) to occur effectively. This causes multipath reflection interference to be developed effectively, and the absorption properties for absorbing light having a particular wavelength are produced. Also in the present embodiment, average complex refractive index (effective complex refractive index) of the first reflector 10 and/or second reflector 30 varies with the specimen. That is, the multipath interference conditions, hence the absorption properties vary with the specimen. Thus, the analysis of the specimen may be performed in the same manner as in the first embodiment.

The sensor S4 according to the present embodiment is structured in the manner as described above.

That is the basic structure of the present embodiment is identical to that of the first embodiment, except that the translucent body is constituted by the translucent porous body having a plurality of pores 21 which is open at the face on the side of the first reflector 10, and the first reflector is constituted by the metal layer formed along the surface contour of the translucent porous body with a plurality of pores 16. Therefore, the present embodiment may provide similar advantageous effects to those of the first embodiment.

The sensor S4 according to the present embodiment is preferable, since it is produced by anodization. The sensor S4, in which the pores 21 of the translucent body 20 and the pores 16 of the first reflector 10 are arranged substantially regularly, may be readily produced by anodization. These pores, however, may be arranged randomly.

In the present embodiment, only Al is described as the major component of the anodizable metal body 40 used for forming the translucent body 20, but any material may be used as long as it is anodizable and the resultant metal oxide has translucency. For example, Ti, Ta, Hf, Zr, Si, In, Zn, and the like may be used other than Al. The anodizable metal body 40 may include two or more anodizable metals.

In the present invention, description has been made in which the second reflector has perfect reflection properties as an example. Alternatively, the translucent body 20 having pores 21 running therethrough may be produced by anodizing the entire portion of the anodizable metal body 40, or anodizing a portion of the anodizable metal body 40 and removing the non-anodized portion 42 and adjacent portion thereof. If a second reflector 30 is formed along the surface contour of the translucent body 20 having the pores 21 running therethrough, then a second reflector 30 having pores and semi-transmissive and semi-reflective properties like the first reflector 10 may be obtained. Thereby the analysis may be performed in the same manner as in the second embodiment.

Fifth Embodiment of the Sensor

Figure 6:
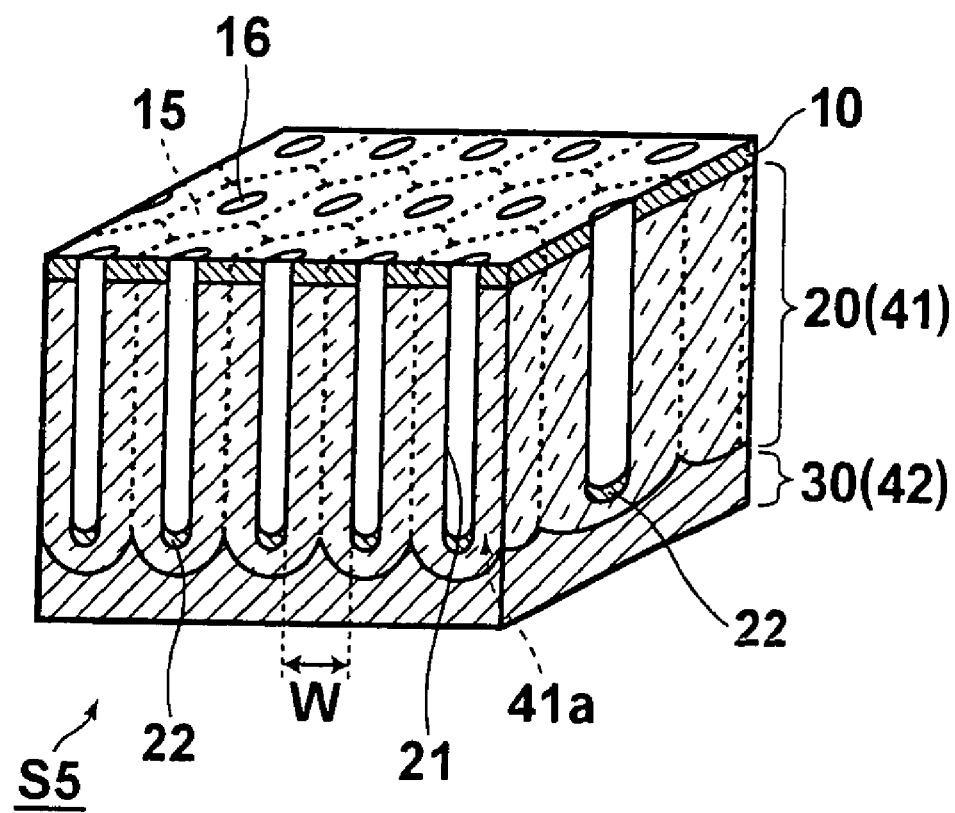
FIG. 6 is a perspective view of the sensor according to a fifth embodiment of the present invention.

Hereinafter, the sensor according to a fifth embodiment of the present invention will be described with reference to FIG. 6. FIG. 6 is a perspective view of the sensor. In the present embodiment, components identical to those of the fourth embodiment are given the same reference symbols and will not be elaborated upon further here.

The basic structure of the sensor S5 according to the present is identical to that of the sensor S4 according to the fourth embodiment, except that each of the plurality of pores 21 formed in the translucent body 20 has a metal 22 at the bottom.

For example, when forming the first reflector 10 by metal vapor deposition, the metal 22 of the same metal forming the first reflector 10 may be filled on the bottom of each of the pores 21 by forming the first reflector 10 under the condition in which the metal is also vapor deposited therein simultaneously.

Alternatively, the metal 22 filled on the bottom of each of the pores 21 of the translucent body 20 may be provided by a different metal from the first reflector 10 by first performing the simultaneous formation of the first reflector 10 and deposition of the metal 22 in the manner as described above, then removing the first reflector 10 and again forming the first reflector 10 by metal vapor deposition using a different metal.

The deposition of the metal 22 may be performed in the same manner as the formation of the first reflector 10, so that metals identical to those for forming the first reflector 10 described in the first embodiment may be used. That is, any metals may be use as the metal 22, including Au, Ag, Cu, Al, Pt, Ni, Ti, alloys of these, and the like. The metal 22 may include two or more different metals described above.

In the present embodiment, multipath reflection (resonance) occurs effectively between the first reflector 10 and the second reflector 30 as in the fourth embodiment. Thereby multipath reflection interference occurs effectively, and the absorption properties for absorbing light having a particular wavelength are produced. Also in the present embodiment, the average complex refractive index (effective complex refractive index) of the first reflector 10 and/or second reflector 30 varies with the specimen. That is, the multipath interference conditions, hence the absorption properties vary with the specimen. Thus, the analysis of the specimen may be performed in the same manner as in the fourth embodiment.

Further, in the present embodiment, local plasmon resonances may be induced on at least one of the surfaces of first reflector 10, second reflector 20, and metal 22 partially filled in each of a plurality of pores 21 of the translucent body 20. In particular, the inventors of the present invention have found that the local plasmon resonances may be induced effectively on the surface of the metal 22 partially filled in each of a plurality of pores of the translucent body 20.

The present embodiment may provide a sensor in which the properties of the measuring light L1 are changed by absorption properties due to the optical interference effects described above, and the local plasmon resonances as in the first embodiment. In such sensor, the analysis of a specimen may be performed by detecting both physical properties 1 of the measuring light L2 that vary according to the absorption properties due to the optical interference effects, and physical properties 2 of the measuring light L2 that vary according to the local plasmon resonances. Further, it may analyze the specimen by detecting the correlation between the physical properties 1 and physical properties 2.

[Design Changes]

It will be appreciated that the present invention is not limited to the embodiments described above, and various design changes may be made without departing from the spirit of the present invention.

Design changes may be made arbitrarily to the structure of the first reflector 10 and second reflector 30, and the combination thereof. For example, sensors according to the present invention may be produced by combining the first to fourth embodiments in various ways to form the first reflector 10 and second reflector 30.

[Multichannel Sensor]

Figure 7A:
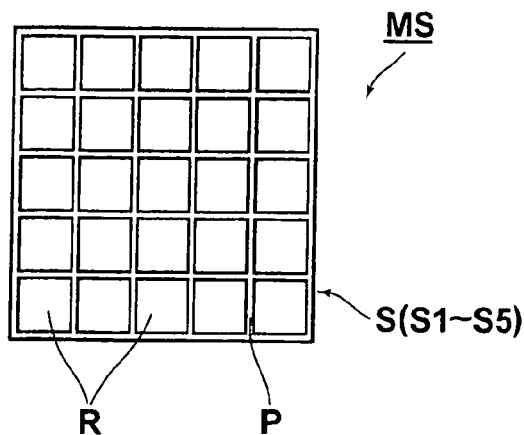
FIG. 7A is an overall plan view of the multichannel sensor according to an embodiment of the present invention.

Hereinafter, the multichannel sensor according to an embodiment of the present invention will be described with reference to FIGS. 7A to 7D. FIG. 7A is an overall plan view of the multichannel sensor.

The multichannel sensor MS according to the present embodiment is constituted by a sensor S which is any of the sensors S1 to S5 according to the embodiment described above. Further, the surface of the sensor S is divided into a plurality of sensor regions R, each of which is to be brought into contact with each of a plurality of specimen. In the present embodiment, the plurality of sensor regions R is disposed two dimensionally in a matrix on the surface of the sensor S. Preferably, adjacent sensor regions R are separated by a partition material P made of a water repellent resin or the like. In the multichannel sensor MS according to the present embodiment, the physical properties of the output light L2 that vary according to the absorption properties are detected by each of the sensor regions R to allow simultaneous analysis of a plurality of specimens.

Figure 7B:
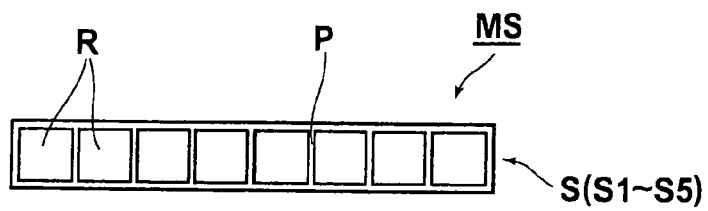
FIG. 7B is a drawing illustrating an example of design change of the multichannel sensor of the present invention.

The shape and arrangement of the sensor regions R on the sensor S are not limited to those described above. The sensor regions R may have any shape or arrangement pattern. For example, sensor regions R may be disposed one dimensionally as shown in FIG. 7B.

Figure 7C:
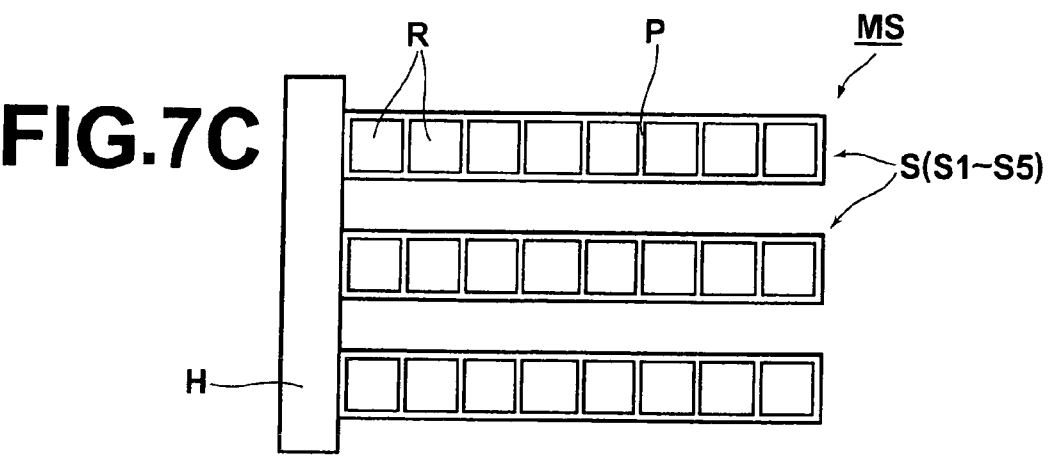
FIG. 7C is a drawing illustrating a further example of design change of the multichannel sensor of the present invention.

In the present embodiment, description has been made in which the multichannel sensor MS is constituted by a single sensor S. But the multichannel sensor MS may be formed by a plurality of sensors S as shown in FIG. 7C. The multichannel sensor MS shown in FIG. 7C is constituted by a plurality of strip shaped sensors S on which the sensor regions R are arranged one dimensionally (like that shown in FIG. 7B) is disposed in the direction substantially parallel to the face of the first reflector 10, which is the light input face, and the plurality of sensors S is held by a single holding member H. The arrangement pattern and holding structure for the plurality of sensors S may be designed arbitrarily.

Figure 7D:
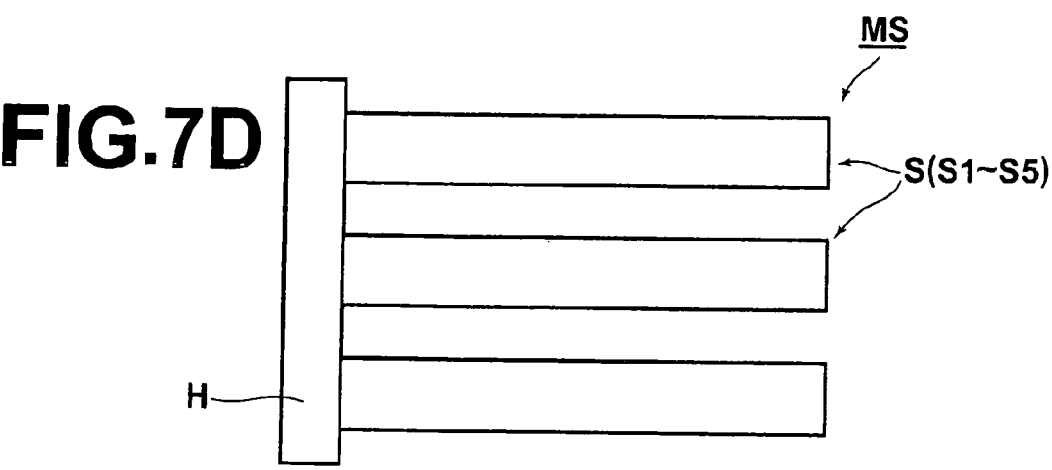
FIG. 7D is a drawing illustrating a still further example of design change of the multichannel sensor of the present invention.

When forming the multichannel sensor MS using a plurality of sensors S, a configuration may be adopted in which each specimen is brought into contact with each sensor S to measure the physical properties of the output light L2 that vary according to the absorption properties by each sensor S without providing a plurality of sensor regions R on each sensor S as shown in FIG. 7D. Such structure may also perform a simultaneous analysis of specimens. In the multichannel sensor MS shown in FIG. 7D, the sensors S may be disposed in accordance with the standard of microwell plate available on the market. In this case, all of the tips of the multichannel sensor MS (right edge in FIG. 7D) may be dipped simultaneously in a plurality of wells of the microwell plate filled with specimens, and analyze them simultaneously.

Embodiment of Sensor with Specimen Cell

Hereinafter, the structure of the sensor with specimen cell according to an embodiment of the present invention will described with reference to FIGS. 8A and 8B. FIG. 8A is a schematic cross-sectional view corresponding to FIG. 1B (hatching for sensor is omitted).

The sensor S is any of the sensors S1 to S5 according to the embodiment described above, and has a device structure that includes the following arranged from the input side of the measuring light L1 in the order listed below: the first reflector 10 having semi-transmissive and semi-reflective properties; translucent body 20; and second reflector 30 having perfect reflection properties, or semi-transmissive and semi-reflective properties.

The sensor S behaves as a reflective type sensor S in which the output light L2 is outputted from the first reflector 10 when the second reflector has perfect reflection properties. When the second reflector has semi-transmissive and semi-reflective properties, the sensor S behaves as any of the following: the reflective type sensor in which the output light L2 is outputted only from the first reflector 10; transmissive type reflector in which the output light L2 is outputted only from the second reflector 30; and semi-transmissive and semi-reflective type sensor in which the output light L2 is outputted from both the first reflector 10 and second reflector 30. The sensor with specimen cell C1 according to the present embodiment may be operable as any type of sensor described above.

The sensor with the specimen cell C1 is the sensor S fixed in a specimen cell 50 such that the first reflector 10 and second reflector 30 are brought into contact with a specimen X within the specimen cell 50 (fixing structure is omitted). The sensor S may be permanently or detachably fixed in the specimen cell 50.

The specimen cell 50 includes a cell body 51 as a major component made of a non-translucent material, such as a metal or the like, capable of holding the specimen X therein. The cell body 51 has translucent windows 52 and 53 fitted therein. The translucent windows 52 and 53 are provided at the sections of the body 51 opposite to the first reflector 10 and second reflector 30 respectively.

In the sensor with the specimen cell C1, the measuring light L1 is inputted to the first reflector 10 from the outside of the specimen cell 50 through the window 52. When it behaves as the reflective type sensor, the reflected light as the output light L2 is outputted to the outside of the specimen cell 50 through the translucent window 52 and detected. When it behaves as the transmissive type sensor, the transmitted light as the output light L2 is outputted to the outside of the specimen cell 50 through the translucent window 53 and detected. When it behaves as the semi-transmissive and semi-reflective type sensor, the reflected light and/or transmitted light as the output light L2 is outputted to the outside of the specimen cell 50 through the translucent window 52 and/or translucent window 53 and detected.

In the present embodiment, the sensor S is fixed in the specimen cell 50 such that the first reflector 10 and second reflector 30 are brought into contact with the specimen X within the specimen cell 50, so that the average complex refractive indices of the first reflector 10 and second reflector 30 vary with the specimen X, thereby the specimen X may be analyzed.

In the present embodiment, analysis for the presence of a particular substance in the specimen and/or the amount thereof may be performed by fixing a binding substance that specifically combines with the particular substance on the first reflector 10 and/or second reflector 30 before filling the specimen X in the specimen cell 50. Example combinations of the particular substance and binding substance may include the combination of antigen and antibody (either may be the binding substance) and the like, and the present embodiment may readily perform time-course analysis of antigen-antibody reactions.

The use of the sensor S in the form of the sensor with the specimen cell C1 allows biological analysis and the like to be performed effectively and accurately with ease.

In the present embodiment, structural description has been made in which the translucent windows 52 and 53 are fitted in the cell body 51 at the sections opposite to the first reflector 10 and second reflector 30 respectively. But, for the reflective type sensor or semi-transmissive and semi-reflective type sensor in which the output light L2 is outputted from the first reflector 10, a configuration may be adopted in which at least the translucent window 52 is provided. Further, for the transmissive type sensor or semi-transmissive and semi-reflective type sensor in which the output light L2 is outputted from the second reflector 30, a configuration may be adopted in which at least the translucent window 53 is provided.

Further, for the reflective type sensor or semi-transmissive and semi-reflective type sensor in which the output light L2 is outputted from the first reflector 10, a configuration may be adopted in which the sensor S is fixed to the specimen cell 50 such that only the second reflector 30 is brought into contact with the specimen X within the specimen cell 50, and the reflected light as the output light L2 is detected as shown in FIG. 8B.

Such structure allows specimen analysis without passing the measuring light L1 and the output light L2 through the specimen X, thereby influence on the analysis by the specimen X may be avoided and more accurate specimen analysis may result. For example, if the liquid temperature of the specimen X or the like varies, refractive index of the sensor S contacting the specimen X may vary slightly, if not great, and may influence on the measurement accuracy. In the structure shown in FIG. 8B, the first reflector 10 is not brought into contact with the specimen X, so that the variation in the refractive index of the first reflector 10 due to temperature change or the like is avoided and accurate analysis may result.

[Sensing Apparatus]

The sensing apparatuses according to first to sixth embodiments of the present invention will be described with reference to FIGS. 9A to 9C, and 10A to 10C. Here, a reflective type sensing apparatus that uses a reflective type sensor or a semi-transmissive and semi-reflective type sensor, and detects reflected light will be described as an example.

Each of the sensing apparatuses A1 to A3 shown in FIGS. 9A to 9C is constituted by: a sensor S, which is any of the sensors S1 to S5 according to the embodiments described above; a measuring light irradiation means 60 for irradiating the measuring light L1 on the sensor S; and detection means 70 for detecting physical properties of the reflected light as the output light L2. Here, the combination of the measuring light irradiation means 60 and detection means differs with each other. Identical components in FIGS. 9A to 9C are given the same reference symbols.

In the sensing apparatus A1, the measuring light irradiation means 60 is constituted by a broad light source 61, such as halogen lamp, xenon lamp, or krypton lamp, and the detection means 70 is constituted by a spectrometer 71 and a data processing unit 72. A collimator lens and/or light guide optics including a condenser lens are provided for the measuring light irradiation means 60 as required.

The sensing apparatus A1 performs specimen analysis by irradiating broad light on the sensor S as the measuring light L1 by the measuring light irradiation means 60, obtaining the spectrum of the reflected light as the output light L2, and detecting the absorption peak wavelength $\lambda$ of the light absorbed by the sensor S, or the amount of shift of the absorption peak wavelength $\lambda$ from a reference value (refer to FIG. 1C for spectrum and absorption peak wavelength $\lambda$).

In the sensing apparatus A2, the measuring light irradiation means 60 is constituted by a single wavelength light source 62, such as laser, or light emitting diode, and the detection means 70 is constituted by a light intensity detector 73 and the data processing unit 72. Also in the sensing apparatus A2, a collimator lens and/or light guide optics including a condenser lens are provided for the measuring light irradiation means 60 as required.

The sensing apparatus A2 performs specimen analysis by irradiating single wavelength light on the sensor S as the measuring light L1 by the measuring light irradiation means 60, and obtaining the light intensity of the reflected light as the output light L2. The measuring light L1 may have any wavelength. When attention is focused on an arbitrary wavelength of light, FIG. 1C indicates that the light intensity of the wavelength varies with the specimen. That is, FIG. 1C indicates that specimen analysis may be performed by detecting the light intensity of the output light L2 for the measuring light L1 having any wavelength.

In the sensing apparatus A2, a configuration may be adopted in which the measuring light irradiation means 60 is constituted by a broad light source 61 instead of the single wavelength light source 62, and a wavelength distribution variable means such as a spectrometer capable of selecting only the particular wavelength light from the output light of the light source 61 or the like. Also in this case, the sensing apparatus A1 may perform specimen analysis in the same manner as described above.

In the sensing apparatus A3, the measuring light irradiation means 60 is constituted by the broad light source 61, and a wavelength distribution variable means 63 capable of selecting particular wavelength light from the output light of the light source 61 and changing the wavelength of the particular wavelength light to be selected with time, and the detection means 70 is constituted by the light intensity detector 73 and data processing unit 72. The data processing unit 72 receives the wavelength data of the light having a particular wavelength selected by the wavelength distribution variable means 63, and light intensity data obtained by the light intensity detector 73 to perform data processing. Also in the sensing apparatus A3, a collimator lens and/or light guide optics including a condenser lens are provided for the measuring light irradiation means 60 as required.

The sensing apparatus A3 performs specimen analysis by irradiating single wavelength light on the sensor S as the measuring light L1, and changing the wavelength of the single wavelength light irradiated on the sensor S with time by the measuring light irradiation means 60, measuring variations in the light intensity of the reflected light as the output light L2 with time to obtain a spectrum similar to that shown in FIG. 1C, and detecting the absorption peak wavelength λ of the light absorbed by the sensor S, or the amount of shift of the absorption peak wavelength λ from a reference value.

As described above, specimen analysis may be performed by detecting at least one of the following by the detection means 70: the light intensity of the output light L2, variation thereof, absorption peak wavelength of light absorbed by the sensor S, and the amount of shift thereof.

Figure 10A:
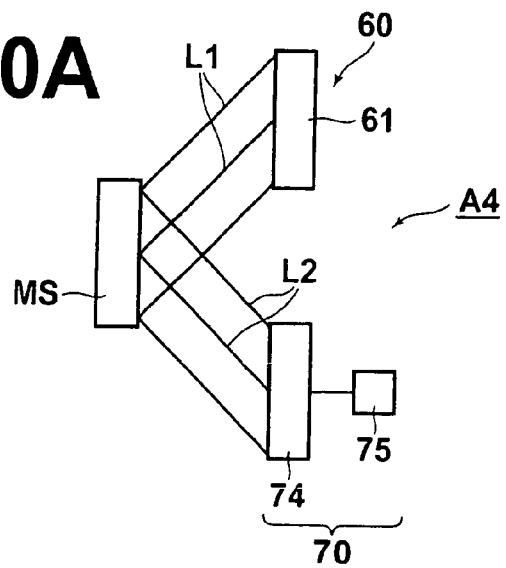
FIG. 10A is a block diagram of the sensing apparatus according to a fourth embodiment of the present invention, illustrating the structure thereof.
Figure 10B:
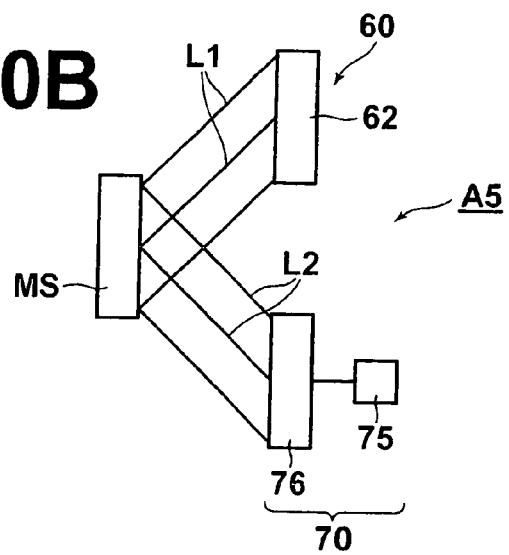
FIG. 10B is a block diagram of the sensing apparatus according to a fifth embodiment of the present invention, illustrating the structure thereof.
Figure 10C:
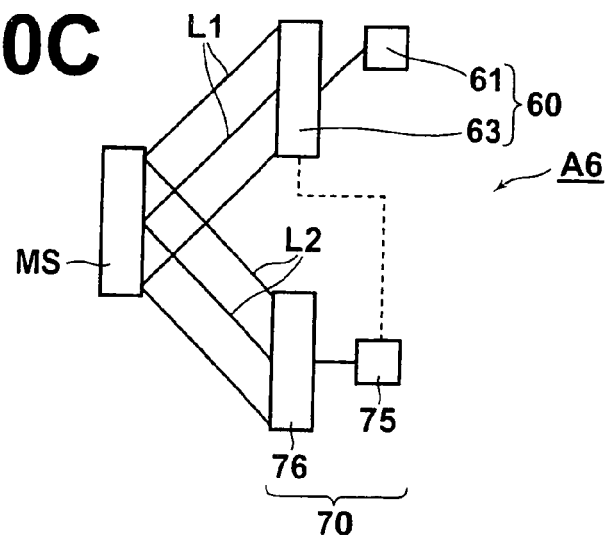
FIG. 10C is a block diagram of the sensing apparatus according to a sixth embodiment of the present invention, illustrating the structure thereof.

Each of the sensing apparatus A4 to A6 shown in FIGS. 10A to 10C is constituted by: the multichannel sensor MS according to the embodiment described above; a measuring light irradiation means 60 for irradiating the measuring light L1 on the entire surface of the multichannel sensor Ms simulataneously; and a detection means 70 for detecting physical properties of the reflected light as the output light L2 with respect to each specimen. Here, the combination of the measuring light irradiation means 60 and detection means differs with each other. Identical components in FIGS. 10A to 10C are given the same reference symbols.

In the sensing apparatus A4, the measuring light irradiation means 60 is constituted by the broad light source 61, such as halogen lamp, xenon lamp, or krypton lamp, and the detection means 70 is constituted by an imaging spectrometer 74 and a data processing unit 75. Light guide optics including a collimator lens for collimating the output light, and the like are provided for the measuring light irradiation means 60 as required.

The sensing apparatus A4 performs simultaneous analysis of a plurality of specimens by irradiating broad light on the entire surface of the multichannel sensor MS simultaneously as the measuring light L1 by the measuring light irradiation means 60, detecting the spectra of the reflected light (output light L2) reflected from a plurality of sensor regions R simultaneously, and detecting the absorption peak wavelength λ of the light absorbed by the multichannel sensor MS with respect to each sensor region R, or the amount of shift of the absorption peak wavelength λ from a reference value (refer to FIG. 1C for spectrum and absorption peak wavelength λ) with respect to each sensor region R.

In the sensing apparatus A5, the measuring light irradiation means 60 is constituted by the single wavelength light source 62, such as laser, or light emitting diode, and the detection means 70 is constituted by a light intensity detector 76 for detecting light intensity distribution, such as image sensor, and the data processing unit 75. Also in the sensing apparatus A5, light guide optics including a collimator lens for collimating the output light, and the like are provided for the measuring light irradiation means 60 as required.

The sensing apparatus A5 performs simultaneous analysis of a plurality of specimens by irradiating single wavelength light on the entire surface of the multichannel sensor MS as the measuring light L1 by the measuring light irradiation means 60, and detecting the light intensity of the reflected light (output light L2) reflected from the plurality of sensor regions R. The measuring light L1 may have any wavelength. When attention is focused on an arbitrary wavelength of light, FIG. 1C indicates that the light intensity of the wavelength varies with the specimen. That is, FIG. 1C indicates that specimen analysis may be performed by detecting the light intensity of the output light L2 for the measuring light L1 having any wavelength.

In the sensing apparatus A5, a configuration may be adopted in which the measuring light irradiation means 60 is constituted by the broad light source 61 instead of the single wavelength light source 62, and a wavelength distribution variable means such as a spectrometer capable of selecting only the particular wavelength light from the output light of the light source 61 or the like. Also in this case, the sensing apparatus A5 may perform simultaneous analysis of a plurality of specimens in the same manner as described above.

In the sensing apparatus A6, the measuring light irradiation means 60 is constituted by the broad light source 61, and wavelength distribution variable means 63 capable of selecting particular wavelength light from the output light of the light source 61 and changing the wavelength of the particular wavelength light to be selected with time, and the detection means 70 is constituted by a light intensity detector 76 for detecting light intensity distribution, such as image sensor, and the data processing unit 75. The data processing unit 75 receives the wavelength data of the light having a particular wavelength selected by the wavelength distribution variable means 63, and light intensity data obtained by the light intensity detector 76 to perform data processing. Also in the sensing apparatus A6, light guide optics including a collimator lens for collimating the output light, and the like are provided for the measuring light irradiation means 60 as required.

The sensing apparatus A6 performs simultaneous analysis of a plurality of specimens by irradiating single wavelength light on the entire surface of the multichannel sensor MS as the measuring light L1, and changing the wavelength of the single wavelength light irradiated on the multichannel sensor MS with time by the measuring light irradiation means 60, measuring variations in the light intensity distribution of the reflected light (output light L1) reflected from the plurality of sensor regions R with time to obtain a spectrum similar to that shown in FIG. 1C with respect to each sensor region R, and detecting the absorption peak wavelength λ of the light absorbed by the multichannel sensor MS or the amount of shift of the absorption peak wavelength λ from a reference value with respect to each sensor region R.

As described above, simultaneous analysis of a plurality of specimens may be performed by detecting at least one of the following by the detection means 70: the light intensity of the output light L2, variation thereof, absorption peak wavelength of light absorbed by the multichannel sensor MS, and the amount of shift thereof.

In the embodiments described above, description has been made with reference to an example case in which the irradiation of the measuring light L1 on the multichannel sensor MS and detection of the output light L2 outputted from the multichannel sensor MS are performed simultaneously. A configuration may be adopted, however, in which the measuring light L1 is scanned and sequentially irradiated on the surface of a plurality of sensor regions R, and the output light L2 is detected sequentially. As for the light scanning means, one or more movable mirrors, such as polygon mirror, galvano mirror, and the like may be used.

It has been already described that when the multichannel sensor MS is constituted by a plurality of sensors S, a configuration may be adopted in which each specimen is brought into contact with each sensor S without providing a plurality of sensor regions R on each sensor S. In such structure, simultaneous analysis of a plurality of specimens may be performed in the same manner as described above by structuring the detection means 70 to perform the detection with respect to each sensor S.

Sensing apparatuses A1 to A6 may analyze refractive index and/or density of a specimen. It may also identify the specimen by analyzing the refractive index thereof. Further, the sensor S or multichannel sensor MS may also analyze presence of a particular substance in the specimen and/or the amount thereof by fixing a binding substance that specifically combines with the particular substance on the side of the sensor S or multichannel sensor MS to be brought into contact with the specimen before bringing the specimen into contact therewith, and irradiating the measuring light L1 on the sensor S or multichannel sensor MS and detecting the output light L2.

Preferably, in the reflective type sensing apparatuses A1 to A6, the detection means 70 is structured to receive and detect only non-mirror reflection component, such as scattered light or the like. The mirror-reflection component has light intensity which is too strong to properly detect the essential properties. Thus, by detecting weak light, such as scattered light or the like, more accurate analysis may be performed. In view of the same reason, in the reflective type sensing apparatuses A1 to A6, it is preferable that the measuring light irradiation means 60 is placed at a position so that the measuring light L1 is irradiated on the sensor S or multichannel sensor MS at an angle other than the normal with respect to the light input surface thereof.

Description has been made with reference to only the reflective type sensing apparatus. In the case of transmissive type sensing apparatus that uses the transmissive type, or semi-transmissive and semi-reflective type sensor S, or multichannel sensor MS, it is only necessary to move the detecting means 70 on the side of the second reflector 30, or the like to allow the detecting means 70 to detect the transmitted light.

EXAMPLES

Hereinafter, examples of the present invention will be described.

Examples 1 and 2

For each of the sensor S4 according to the fourth embodiment (Example 1), and sensor S5 according to the fifth embodiment (Example 2), a simulation was conducted for the reflected light spectrum using electromagnetic field analysis simulation software based on the FD-TD method. The calculations were made on the assumption that water is filled in the pores 21. The following conditions were used in the calculations.

<Conditions for Calculation>
  First Reflector 10: Au (20 nm thickness)
  Translucent Body 20: $Al_2O_3$ (200 nm thickness), Pitch of Pores 21: 100 nm, Pore Diameter of Pores 21: 50 nm
  Second reflector 30: Al
  Metal 22: Au (20 nm thickness) filled in pores 21 in Example 2 sensor
  Measuring Light L1: White Light (Normal Incidence)

The complex refractive index of a substance differs according to the wavelength of the input light. The average complex refractive index of the translucent body 20 was calculated in view of the aperture ratio of the pores 21 and substance filled therein (water for Example 1, water and Au for Example 2). The average complex refractive index of the first reflector 10 was calculated taking into account the aperture ratio of the pores 21. The average complex refractive index of the second reflector 30 is identical to that of Al, since the second reflector has no pore.

Figure 11:
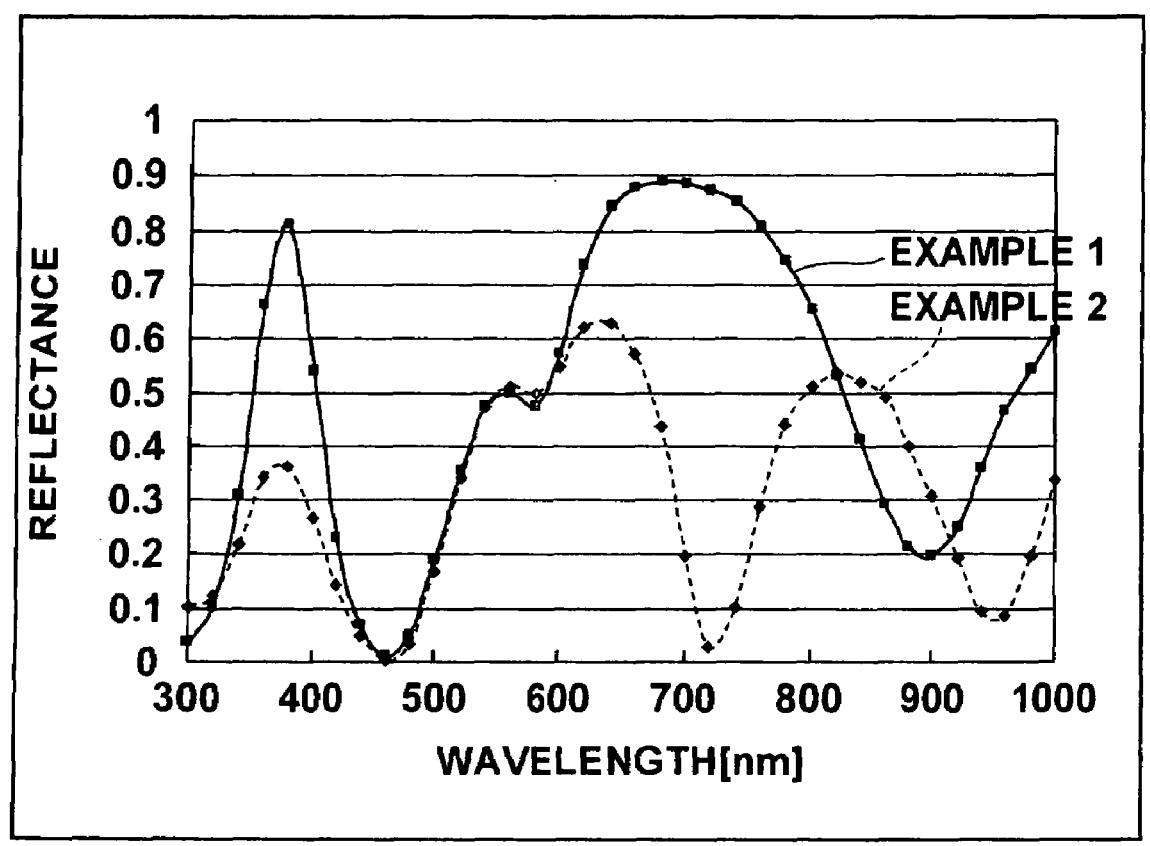
FIG. 11 is a graph illustrating the simulation results of Examples 1 and 2.

The results are shown in FIG. 11.

In Example 1 in which no metal is filled in the pores 21, and in Example 2 in which the metal 22 is filled in the pores 21, the absorption peaks due to multipath interference were observed in the ranges from 400 to 500 nm, and from 850 to 950 nm. In the sensor of Example 2 in which the metal 22 is filled in the pores 21, the absorption peak due to local plasmon resonances was also observed near 700 nm in addition to the absorption peaks due to multipath interference.

The inventors of the present invention have verified that the spectrum may be changed by changing the specimens filled in the pores 21, and thus the specimen analysis may be performed using the sensors of the Example 1 and 2.

INDUSTRIAL APPLICABILITY

The sensors of the present invention may be preferably used as biosensors and the like.

The invention claimed is:

1. A sensor in which measuring light is inputted and outputted therefrom as output light after physical properties thereof are changed by a specimen, and detected, the sensor comprising the following arranged from input side of the measuring light in the order listed below:
   a first reflector having semi-transmissive and semi-reflective properties;
   a translucent body; and a second reflector having perfect reflection properties, or semi-transmissive and semi-reflective properties, wherein:

the first reflector and/or second reflector is brought into contact with the specimen, and the average complex refractive index thereof varies with the specimen;

absorption properties for absorbing light having a particular wavelength are produced according to the average complex refractive index of the first reflector, average complex refractive index of the second reflector, and average complex refractive index and thickness of the translucent body;

the properties of the measuring light are changed by the optical properties including the absorption properties, the output light is outputted from the first reflector and/or second reflector; and the physical properties of the output light that vary according to the optical properties are detected.

2. The sensor according to claim 1, wherein the first reflector and/or second reflector brought into contact with the specimen has a relief structure smaller than the wavelength of the measuring light.

3. The sensor according to claim 2, wherein the first reflector and/or second reflector brought into contact with the specimen is constituted by a metal pattern layer made of a metal formed on the surface of the translucent body in a pattern.

4. The sensor according to claim 3, wherein the properties of the measuring light are changed by the absorption properties and a local plasmon resonance on the metal pattern layer.

5. The sensor according to claim 2, wherein the first reflector and/or second reflector brought into contact with the specimen is constituted by a metal particle layer having a plurality of metal particles fixed on the surface of the translucent body.

6. The sensor according to claim 5, wherein the properties of the measuring light are changed by the absorption properties and a local plasmon resonance on the metal particle layer.

7. The sensor according to claim 2, wherein:

the first reflector is brought into contact with the specimen, and the average complex refractive index thereof varies with the specimen;

the translucent body is constituted by a translucent porous body having a plurality of pores, each of which has a pore diameter substantially smaller than the wavelength of the measuring light and is open at the face on the side of the first reflector; and the first reflector is constituted by a metal layer having a plurality of pores formed along the surface contour of the translucent body.

8. The sensor according to claim 7, wherein the translucent body is constituted by a metal oxide body obtained by anodizing a portion of an anodizable metal body, the second reflector is constituted by the non-anodized portion of the anodizable metal body, and the first reflector is constituted by a metal layer formed on the translucent body.

9. The sensor according to claim 2, wherein:

the first reflector is brought into contact with the specimen, and the average complex refractive index thereof varies with the specimen;

the translucent body is constituted by a translucent porous body having a plurality of pores, each of which has a pore diameter substantially smaller than the wavelength of the measuring light and is open at the face on the side of the first reflector;

the first reflector is constituted by a metal layer having a plurality of pores formed along the surface contour of the translucent body; and a metal is partially filled in each of the plurality of pores of the translucent body.

10. The sensor according to claim 9, wherein the properties of the measuring light are changed by the absorption properties and a local plasmon resonance developed on at least one of the following: the first reflector, second reflector, and metal partially filled in each of the plurality of pores of the translucent body.

11. The sensor according to claim 9, wherein the translucent body is constituted by a metal oxide body obtained by anodizing a portion of an anodizable metal body, the second reflector is constituted by the non-anodized portion of the anodizable metal body, and the first reflector is constituted by a metal layer formed on the translucent body.

12. A multichannel sensor in which measuring light is inputted and outputted therefrom as output light after the physical properties thereof are changed by a plurality of specimens, and detected to allow simultaneous analysis of the plurality of specimens, wherein:

the multichannel sensor includes one or more sensors of claim 1 which are divided into a plurality of sensor regions, each being brought into contact with each of the plurality of specimens; and the physical properties that vary according to the optical properties are detected with respect to each sensor region.

13. A sensing apparatus comprising:

the multichannel sensor of claim 12;

a measuring light irradiation means for irradiating the measuring light on the multichannel sensor; and a detection means for detecting the physical properties of the output light.

14. The sensing apparatus according to claim 13, wherein the detection means detects at least one of the following: the light intensity of the output light, variation thereof, absorption peak wavelength of light absorbed by the sensor, and the amount of shift thereof.

15. A sensing method using the multichannel sensor of claim 12, the method comprising the steps of:

fixing a binding substance that specifically combines with a particular substance on the side of the multichannel sensor to be brought into contact with the specimen before bringing the specimen into contact therewith;

irradiating the measuring light on the multichannel sensor; and detecting the physical properties of the output light to analyze the presence of the particular substance and/or amount thereof in the specimen.

16. A multichannel sensor in which measuring light is inputted and outputted therefrom as output light after the physical properties thereof are changed by a plurality of specimens, and detected to allow simultaneous analysis of the plurality of specimens, wherein:

the multichannel sensor includes a plurality of the sensors of claim 1, and the physical properties that vary according to the optical properties are detected with respect to each sensor.

17. A sensing apparatus comprising:

the multichannel sensor of claim 16;

a measuring light irradiation means for irradiating the measuring light on the multichannel sensor; and a detection means for detecting the physical properties of the output light.

18. The sensing apparatus according to claim 17, wherein the detection means detects at least one of the following: the light intensity of the output light, variation thereof, absorption peak wavelength of light absorbed by the sensor, and the amount of shift thereof.

19. The sensing apparatus according to claim 17, wherein:
the sensor outputs the output light at least from the first reflector; and
the detection means receives only non-mirror reflection component of the output light and detects the physical properties.

20. The sensing apparatus according to claim 17, wherein the measuring light irradiation means is placed at a position so that the measuring light is irradiated on the sensor at an angle other than the normal with respect to the light input face of the sensor.

21. The sensing apparatus according to claim 17, wherein the apparatus analyzes the refractive index and/or density of the specimen.

22. A sensing method using the multichannel sensor of claim 16, the method comprising the steps of:
fixing a binding substance that specifically combines with a particular substance on the side of the multichannel sensor to be brought into contact with the specimen before bringing the specimen into contact therewith;
irradiating the measuring light on the multichannel sensor; and
detecting the physical properties of the output light to analyze the presence of the particular substance and/or amount thereof in the specimen.

23. A sensor with specimen cell, comprising the sensor of claim 1 which is attached to a specimen cell fillable with the specimen, wherein the sensor is fixed to the specimen cell such that the first reflector and/or second reflector of the sensor is brought into contact with the specimen in the specimen cell.

24. A sensing apparatus comprising:
the sensor of claim 1;
a measuring light irradiation means for irradiating the measuring light on the sensor; and
a detection means for detecting the physical properties of the output light.

25. The sensing apparatus according to claim 24, wherein the detection means detects at least one of the following: the light intensity of the output light, variation thereof, absorption peak wavelength of light absorbed by the sensor, and the amount of shift thereof.

26. The sensing apparatus according to claim 24, wherein the measuring light irradiation means is placed at a position so that the measuring light is irradiated on the sensor at an angle other than the normal with respect to the light input face of the sensor.

27. The sensing apparatus according to claim 24, wherein the apparatus analyzes the refractive index and/or density of the specimen.

28. The sensing apparatus according to claim 24, wherein the apparatus identifies the specimen by analyzing the refractive index thereof.

29. A sensing method using the sensor according to claim 1, the method comprising the steps of:
fixing a binding substance that specifically combines with a particular substance on the side of the sensor to be brought into contact with the specimen before bringing the specimen into contact therewith;
irradiating the measuring light on the sensor; and
detecting the physical properties of the output light to analyze the presence of the particular substance and/or amount thereof in the specimen.

* * * * *